(12) United States Patent
Chen

(10) Patent No.: US 7,408,068 B2
(45) Date of Patent: *Aug. 5, 2008

(54) COMPOUNDS FOR THE TREATMENT OF NEURODEGENERATIVE DISORDERS

(75) Inventor: Yuhpyng L. Chen, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/778,773

(22) Filed: Jul. 17, 2007

(65) Prior Publication Data

US 2007/0270426 A1 Nov. 22, 2007

Related U.S. Application Data

(63) Continuation of application No. 10/922,425, filed on Aug. 20, 2004, now Pat. No. 7,253,195.

(60) Provisional application No. 60/496,735, filed on Aug. 21, 2003.

(51) Int. Cl.
*A61K 31/433* (2006.01)
*C07D 285/135* (2006.01)

(52) U.S. Cl. ...................... 548/139; 514/363

(58) Field of Classification Search .................. 548/139
See application file for complete search history.

(56) References Cited

U.S. PATENT DOCUMENTS 6,323,315 B1 11/2001 Pettit et al.

7,253,195 B2 8/2007 Chen

FOREIGN PATENT DOCUMENTS

WO WO2001/81298 11/2001

OTHER PUBLICATIONS

Thompson, et al., "Protein Conformational Misfolding And Amyloid Formation: Characteristics Of A New Class Of Disorders That Include Alzheimer's And Prion Diseases," *Current Medicinal Chemistry*, 2002, 1751-1762, vol. 9, No. 19.
Brown, et al., "Drug Therapy In Human And Experimental Transmissible Spongiform Encephalopathy," *Neurology*, 2002, 1720-1725, vol. 58, No. 12.
Petit, et al., CA 134:237837, 2001.

*Primary Examiner*—Laura L. Stockton
(74) *Attorney, Agent, or Firm*—Jeffrey H. Tidwell; Bryan C. Zielinski

(57) ABSTRACT

The present invention relates to compounds of the Formula

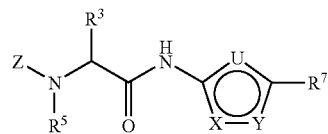

I wherein $R^3$, $R^5$, $R^7$, U, X, Y and Z are as defined. Compounds of the Formula I have activity inhibiting production of Aβ-peptide. This invention also relates to pharmaceutical compositions and methods of treating diseases, for example, neurodegenerative diseases, e.g., Alzheimer's disease, in a mammal comprising compounds of the Formula I.

19 Claims, No Drawings

COMPOUNDS FOR THE TREATMENT OF NEURODEGENERATIVE DISORDERS

CROSS REFERENCE TO RELATED APPLICATION

This application is a continuation of U.S. patent application Ser. No. 10/922,425, filed Aug. 20, 2004, now U.S. Pat. No. 7,253,195, which claims the benefit of U.S. patent application Ser. No. 60/496,735, filed Aug. 21, 2003.

FIELD OF THE INVENTION

The present invention relates to the treatment of Alzheimer's disease and other neurodegenerative and/or neurological disorders in mammals, including humans. This invention also relates to inhibiting, in mammals, including humans, the production of Aβ-peptides that can contribute to the formation of neurological deposits of amyloid protein. More particularly, this invention relates to oxazole compounds useful for the treatment of neurodegenerative and/or neurological disorders, such as Alzheimer's disease and Down's Syndrome, related to Aβ-peptide production.

BACKGROUND OF THE INVENTION

Dementia results from a wide variety of distinctive pathological processes. The most common pathological processes causing dementia are Alzheimer's disease (AD), cerebral amyloid angiopathy (CM) and prion-mediated diseases (see, e.g., Haan et al. *Clin. NeuroL. Neurosurg.* 1990, 92(4):305-310; Glenner et al. *J Neurol. Sci.* 1989, 94:1-28). AD affects nearly half of all people past the age of 85, the most rapidly growing portion of the United States population. As such, the number of AD patients in the United States is expected to increase from about 4 million to about 14 million by the middle of the next century.

Treatment of AD typically is the support provided by a family member in attendance. Stimulated memory exercises on a regular basis have been shown to slow, but not stop, memory loss. A few drugs, for example Aricep™, provide treatment of AD.

A hallmark of AD is the accumulation in the brain of extracellular insoluble deposits called amyloid plaques and abnormal lesions within neuronal cells called neurofibrillary tangles. Increased plaque formation is associated with an increased risk of AD. Indeed, the presence of amyloid plaques, together with neurofibrillary tangles, are the basis for definitive pathological diagnosis of AD.

The major components of amyloid plaques are the amyloid Aβ-peptides, also called Aβ-peptides, which consist of three proteins having 40, 42 or 43 amino acids, designated as the $A\beta_{1-40}$, $A\beta_{1-42}$ and $A\beta_{1-43}$ peptides, respectively. The Aβ-peptides are thought to cause nerve cell destruction, in part, because they are toxic to neurons in vitro and in vivo.

The Aβ peptides are derived from larger amyloid precursor proteins (APP proteins), which consist of four proteins containing 695, 714, 751 or 771 amino acids, designated as the $APP_{695}$, $APP_{714}$, $APP_{751}$ and $APP_{771}$, respectively. Proteases are believed to produce the Aβ peptides by cleaving specific amino acid sequences within the various APP proteins. The proteases are named "secretases" because the Aβ-peptides they produce are secreted by cells into the extracellular environment. These secretases are each named according to the cleavage(s) they make to produce the Aβ-peptides. The secretase that forms the amino terminal end of the Aβ-peptides is called the beta-secretase. The secretase that forms the carboxyl terminal end of the Aβ-peptides is called the gamma-secretase (Haass, C. and Selkoe, D. J. 1993 *Cell* 75:1039-1042).

This invention relates to novel compounds that inhibit Aβ-peptide production, to pharmaceutical compositions comprising such compounds, and to methods of using such compounds to treat neuorodegenerative and/or neurological disorders.

SUMMARY OF THE INVENTION

The present invention relates to compounds of the formula I

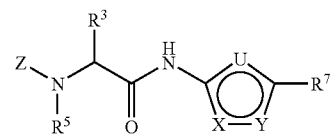

The ring containing X, Y, U is an aromatic ring in which one of the X, Y, U is a S and the other two of the X, Y, U are N as shown below I-A to I-C.

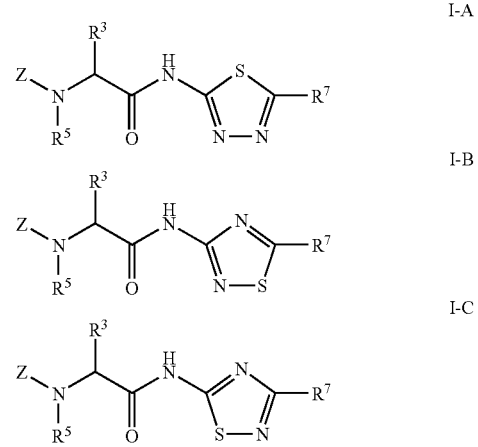

wherein Z is selected from —C(=O)CHR$^1$R$^2$, —C(=S)CHR$^1$R$^2$, —(C=NR$^8$)CHR$^1$R$^2$, —C(=O)C(=O)R$^1$ and —S(O)$_2$—R$^1$;

R$^1$ is selected from —C$_1$-C$_{20}$ alkyl, —C$_2$-C$_{20}$ alkenyl, —C$_2$-C$_{20}$ alkynyl, —C$_4$-C$_{20}$ alkoxy, C$_2$-C$_{20}$ alkenoxy, —C$_2$-C$_{20}$ alkynoxy, —C$_3$-C$_{20}$ cycloalkyl, —C$_4$-C$_{20}$ cycloalkenyl, (C$_{10}$-C$_{20}$)bi- or tricycloalkyl, (C$_{10}$-C$_{20}$)bi- or tricycloalkenyl, (4-20 membered) heterocycloalkyl, —C$_6$-C$_{20}$ aryl and (5-20 membered) heteroaryl;

wherein R$^1$ is optionally independently substituted with from one to six fluorine atoms or with from one to three substituents independently selected from the group R$^{1a}$;

R$^{1a}$ is in each instance independently selected from —OH, —C$_1$-C$_{12}$ alkyl, —C$_2$-C$_{12}$ alkenyl, —C$_2$-C$_{12}$ alkynyl, —C$_1$-C$_6$ alkoxy, —C$_2$-C$_6$ alkenoxy, —C$_2$-C$_6$ alkynoxy, —CF$_3$, —OCF$_3$, —Cl, —Br, —I, —CN, —NO$_2$, —NR$^9$R$^{10}$, —C(=O)NR$^9$R$^{10}$, —SO$_2$—NR$^9$R$^{10}$, —C(=O)R$^{11}$, —S(O)$_n$—R$^{11}$, —C(=O)OR$^{12}$, —C$_3$-C$_{15}$ cycloalkyl, —C$_4$-C$_{15}$ cycloalkenyl, —(C$_5$-C$_{11}$)bi- or tricycloalkyl, —(C$_7$-C$_{11}$) bi- or tricycloalkenyl, -(4-20 membered) heterocycloalkyl, —C$_6$-C$_{15}$ aryl, -(5-15 membered) heteroaryl, —C$_6$-C$_{15}$ aryloxy and -(5-15 membered) heteroaryloxy, wherein said cycloalkyl, cycloalkenyl, bi- or tricycloalkyl, bi- or tricycloalkenyl, heterocycloalkyl, aryl, heteroaryl, aryloxy and heteroaryloxy are each optionally independently substituted with from one to three substituents independently selected from the group $R^{1b}$;

$R^{1b}$ is in each instance independently selected from —OH, —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —$NO_2$, —$NR^9R^{10}$, —C(=O)$NR^9R^{10}$, —C(=O)$R^{11}$, —S(O)$_n$—$R^{11}$, —$C_6$-$C_{15}$ aryloxy and -(5-15 membered) heteroaryloxy, wherein said alkyl, alkenyl and alkynyl are each optionally independently substituted with from one to six fluorine atoms or with from one to two substituents independently selected from —$C_1$-$C_4$ alkoxy, or with a hydroxy group;

$R^9$ and $R^{10}$ are in each instance each independently selected from —H, —$C_1$-$C_{12}$ alkyl, —$C_2$-$C_{12}$ alkenyl, —$C_2$-$C_{12}$ alkynyl, —$CF_3$, —C(=O)$R^{11}$, —S(O)$_n$—$R^{11}$, —C(=O)$OR^{12}$, —C(=O)$NR^{11}R^{12}$, —$SO_2$—$NR^{11}R^{12}$, —($C_{zero}$-$C_4$ alkylene)-($C_3$-$C_{20}$ cycloalkyl), —($C_{zero}$-$C_4$ alkylene)-($C_4$-$C_8$ cycloalkenyl), —$C_{zero}$-$C_4$ alkylene)-($C_5$-$C_{11}$) bi- or tricycloalkyl), —($C_{zero}$-$C_4$ alkylene)-(($C_7$-$C_{11}$)bi- or tricycloalkenyl), —($C_{zero}$-$C_4$ alkylene)-((5-10 membered) heterocycloalkyl), ($C_{zero}$-$C_4$ alkylene)-($C_6$-$C_{10}$ aryl) and —($C_{zero}$-$C_4$ alkylene)-((510 membered) heteroaryl), wherein said aryl, heteroaryl, alkyl, alkenyl and alkynyl are each optionally independently substituted with from one to six fluorine atoms or with from one to two substitutents independently selected from —$C_1$-$C_4$ alkoxy, or with a hydroxy group, and wherein said cycloalkyl, cycloalkenyl, bi- or tricycloalkyl, bi- or tricycloalkenyl, heterocycloalkyl, aryl and heteroaryl are each optionally independently substituted with from one to three substituents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —$NO_2$, —$CF_3$, —$NH_2$, —C(=O)$NH_2$, —$SO_2$—$NR^9R^{10}$, —C(=O)H and —C(=O)OH, wherein said alkyl, alkenyl and alkynyl substituents are each optionally independently further substituted with from one to six fluorine atoms or with from one to two substituents independently selected from —$C_1$-$C_4$ alkoxy, or with a hydroxy group;

or $NR^9R^{10}$ may in each instance independently optionally form a heterocycloalkyl moiety of from four to ten ring members, said heterocycloalkyl moiety optionally containing one to two further heteroatoms independently selected from N, O and S, and optionally containing from one to three double bonds, wherein the carbon atoms of the heterocycloalkyl moiety of $NR^9R^{10}$ are optionally independently substituted with from one to three substituents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —F, —Cl, —Br, —I, —$CF_3$, —$NH_2$, —C(=O)$NH_2$, —$O_2$—$NH_2$, —C(=O)$R^{11}$, —S(O)$_n$—$R^{11}$, ($C_{zero}$-$C_4$ alkylene)-($C_6$-$C_{10}$ aryl), ($C_{zero}$-$C_4$ alkylene)-((5-10 membered heteroaryl), ($C_{zero}$-$C_4$ alkylene)-($C_6$-$C_{10}$ cycloalkyl) and ($C_{zero}$-$C_4$ alkylene)-(5-10 membered) heterocycloakyl, and wherein the ($C_{zero}$-$C_4$ alkylene)-((5-10 membered) heterocycloalkyl) substituent and the nitrogen atoms of said heterocycloalkyl moiety of $NR^9R^{10}$ are each optionally independently substituted with one substituent independently selected from —$C_1$-$C_{12}$ alkyl, —$C_2$-$C_{12}$ alkenyl, —$C_2$-$C_{12}$ alkynyl, —C(=O)$NH_2$, —$SO_2$—$NH_2$, C(=O)$R^{11}$, —S(O)$_n$—$R^{11}$, ($C_{zero}$-$C_4$ alkylene)-($C_6$-$C_{10}$ aryl), ($C_{zero}$-$C_4$ alkylene)-((5-10 membered) heteroaryl), ($C_{zero}$-$C_4$ alkylene)-($C_6$-$C_{10}$ cycloalkyl) and ($C_{zero}$-$C_4$ alkylene)-((5-10 membered) heterocycloalkyl), and wherein said alkyl, alkenyl and alkynyl substituents are each optionally independently further substituted with from one to six fluorine atoms, or with from one to two substituents independently selected from —$C_1$-$C_4$ alkoxy, or with a hydroxy group;

$R^{11}$ and $R^{12}$ are in each instance each independently selected from —$C_1$-$C_{15}$ alkyl, —$C_2$-$C_6$ alkenyl, —$C_2$-$C_6$ alkynyl, —($C_{zero}$-$C_4$ alkylene)-($C_3$-$C_{15}$ cycloalkyl), —$C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkenyl), —($C_{zero}$-$C_4$ alkylene)-($C_6$-$C_{15}$ aryl), —($C_{zero}$-$C_4$ alkylene)-((5-15 membered) heterocycloalkyl) and —($C_{zero}$-$C_4$ alkylene)-((5-15 membered) heteroaryl);

wherein $R^{11}$ and $R^{12}$ are each optionally independently substituted with from one to three substituents independently selected from the group $R^{1b}$;

$R^2$ is selected from —H, —OH, —$NH_2$, —$CH_2OH$, —OC(=O)$CH_3$, —C($CH_3$)$_2$OH, —C($CH_3$)($CH_2CH_3$)(OH), —C(OH)($C_{zero}$-$C_4$ alkyl)($C_{zero}$-$C_4$ alkyl), —OC(=O)$R^4$ and —OC(=O)$OR^4$, wherein said —OC(=O)$R^4$ and —OC(=O)$OR^4$ may optionally be a prodrug of the corresponding OH of $R^2$;

$R^3$ is selected from —$C_1$-$C_6$ alkyl, —$C_2$-$C_6$ alkenyl, —$C_2$-$C_6$ alkynyl and —($C_{zero}$-$C_4$ alkylene)-($C_3$-$C_6$ cycloalkyl), wherein when $R^3$ is alkyl, alkenyl or alkynyl, $R^3$ is optionally independently substituted with a substituent independently selected from —$C_1$-$C_4$ alkoxy, —OH, —F and —S($C_1$-$C_4$ alkyl);

$R^4$ is selected from —$C_1$-$C_4$ alkyl, —CH(OH)($C_1$-$C_4$ alkyl), —CH(OH)($C_5$-$C_6$ aryl), —CH(OH)((5-6 membered) heteroaryl), —CH(OH)($C_5$-$C_6$ cycloalkyl), —CH(OH)((5-6 membered) heterocycloalkyl);

$R^5$ is selected from —H, —$C_1$-$C_4$ alkyl, —$C_2$-$C_4$ alkenyl, —$C_2$-$C_4$ alkynyl, —C(=O)($C_1$-$C_4$ alkyl), —$C_6$-$C_{10}$ aryl, -(5-20 membered) heteroaryl, —$SO_2$—($C_6$-$C_{10}$ aryl), —$SO_2$-((5-20 membered) heteroaryl), —$SO_2$—$CH_2$—($C_6$-$C_{20}$ aryl) and —$SO_2$—$CH_2$-((5-20 membered) heteroaryl);

$R^7$ is selected from —H, —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_2$-$C_{20}$ alkynoxy, —F, —Cl, —Br, —I, —CN, —$NO_2$, —OH, —$CF_3$, —$NR^9R^{10}$, —($C_1$-$C_{11}$ alkylene)-$NR^9R^{10}$, —C(=O)$NR^9R^{10}$, —C(=O)$R^{11}$, —CHO, —S(O)$_n$—$R^{11}$, —C(=O)$OR^{12}$, —($C_{zero}$-$C_4$ alkylene)-($C_3$-$C_{20}$ cycloalkyl), —($C_{zero}$-$C_4$ alkylene)-($C_4$-$C_{20}$ cycloalkenyl), —($C_{zero}$-$C_4$ alkylene)-(($C_{10}$-$C_{20}$)bi- or tricycloalkyl), —($C_{zero}$-$C_4$ alkylene)-(($C_{10}$-$C_{20}$)bi- or tricycloalkenyl), —($C_{zero}$-$C_4$ alkylene)-((3-20 membered) heterocycloalkyl), —($C_{zero}$-$C_4$ alkylene)-($C_6$-$C_{15}$ aryl), —($C_{zero}$-$C_{11}$ alkylene)-(C(=O)$R^{11}$, —($C_1$-$C_{11}$ alkylene)-(COOH), —($C_{zero}$-$C_{11}$alkylene)-CHO, —$SO_2NR^9R^{10}$, —S—($C_1$-$C_{20}$alkylene)(C(=O)$OR^8$, —S—($C_1$-$C_{20}$alkylene)-O—($C_1$-$C_{11}$alkyl), —S—($C_1$-$C_{20}$alkylene)-O—($C_5$-$C_{11}$aryl), —$SO_2NR^9R^{10}$, —S—($C_1$-$C_{20}$alkylene)-$NR^9R^{10}$, —($C_1$-$C_{11}$ alkylene)-O—($C_{zero}$-$C_4$alkylene)-O—($C_6$-$C_{11}$aryl), and —($C_{zero}$-$C_4$ alkylene)-((5-15 membered) heteroaryl), wherein said heterocycloalkyl optionally contains from one to four double or triple bonds;

wherein $R^7$ is optionally substituted with from one to six fluorine atoms or with from one to three substituents independently selected from the group $R^{1a}$;

$R^8$ is selected from —H and —$C_1$-$C_6$ alkyl;

or, when Z is —C(=$NR^8$)$CHR^1R^2$, $R^8$ and $R^1$ may together with the nitrogen and carbon atoms to which they are respectively attached optionally form a five to fourteen membered heteroaryl ring or a five to eight membered heterocycloalkyl ring, wherein said heteroaryl or heterocycloalkyl ring optionally contains from one to two further heteroatoms selected from N, O and S, and wherein said heterocycloalkyl ring optionally contains from one to three double bonds, and wherein said heteroaryl or heterocycloalkyl ring is optionally substituted with from one to three substituents independently selected from the group $R^{1b}$;

n is 0, 1, 2 and the pharmaceutically acceptable salts of such compounds.

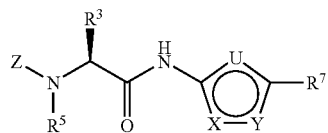

In another embodiment, the compound of Formula I has the following structure:

Compounds of the Formula I may have optical centers and therefore may occur in different enantiomeric, diastereomeric and meso configurations. The present invention includes all enantiomers, diastereomers, and other stereoisomers of such compounds of the Formula I, as well as racemic and other mixtures thereof. The present invention also includes all tautomers of the Formula I. When the compounds of Formula I of the present invention contain one optical center, the "S" enantiomer is preferred.

Insofar as the compounds of Formula I of this invention contain basic groups, they can form acid addition salts with various inorganic and organic acids. The present invention also relates to the pharmaceutically acceptable acid addition salts of compounds of the Formula I. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent, and thereafter, convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts. Other examples of pharmaceutically acceptable salts of the compounds of this invention are the salts of salicylic acid, oxalic acid, di-p-toluoyl tartaric acid, mandelic acid, sodium, potassium, magnesium, calcium and lithium.

The present invention also includes isotopically-labeled compounds that are identical to those recited in Formula I, but for the fact that one or more atoms are replaced by an atom having an atomic mass or mass number different from the atomic mass or mass number usually found in nature. Examples of isotopes that can be incorporated into the compounds of the present invention include isotopes of hydrogen, carbon, nitrogen, oxygen, phosphorous, fluorine, chlorine and iodine, such as $^2H$, $^3H$, $^{13}C$, $^{11}C$, $^{14}C$, $^{15}N$, $^{18}O$, $^{17}O$, $^{18}F$, $^{123}I$ and $^{125}I$, respectively. The compounds of Formula I of the present invention, prodrugs thereof, pharmaceutically acceptable salts of such compounds or of such prodrugs, and compounds and derivatives of such compounds that contain the aforementioned isotopes and/or other isotopes are within the scope of this invention. Such compounds may be useful as research and diagnostic tools in metabolism pharmacokinetic studies and in binding assays. Certain isotopically-labeled compounds of the Formula I of the present invention, for example, those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of the Formula I of the present invention and prodrugs and derivatives thereof may generally be prepared by carrying out the procedures disclosed in the schemes and discussion of the schemes and/or in the examples and preparations described herein, by substituting a readily available isotopically-labeled reagent for a nonisotopically-labeled reagent in the preparation of said compounds.

Unless otherwise indicated, as used herein, the terms "halogen" and "halo" include F, Cl, Br and I.

Unless otherwise indicated, as used herein, the term "alkyl" includes saturated monovalent hydrocarbon radicals having straight or branched moieties. Examples of alkyl groups include, but are not limited to, methyl, ethyl, n-propyl, isopropyl, cyclopropylmethylene (—$CH_2$Cyclopropyl) and t-butyl.

Unless otherwise indicated, as used herein, the term "alkenyl" includes alkyl moieties having at least one carbon-carbon double bond wherein alkyl is as defined above. Examples of alkenyl include, but are not limited to, ethenyl and propenyl.

Unless otherwise indicated, as used herein, the term "alkynyl" includes alkyl moieties having at least one carbon-carbon triple bond wherein alkyl is as defined above. Examples of alkynyl groups include, but are not limited to, ethynyl and 2-propynyl.

Unless otherwise indicated, as used herein, the term "alkoxy", means "alkyl-O—", wherein "alkyl" is as defined above. Examples of "alkoxy" groups include, but are not limited to, methoxy, ethoxy, propoxy, butoxy, pentoxy and allyloxy.

Unless otherwise indicated, as used herein, the term "alkenoxy", means "alkenyl-O—", wherein "alkenyl" is as defined above.

Unless otherwise indicated, as used herein, the term "alkynoxy", means "alkynyl-O—", wherein "alkynyl" is as defined above.

In all of the above defined "$C_1$-$C_x$ alkyl," "$C_1$-$C_x$ alkenyl," "$C_1$-$C_x$ alkynyl," "$C_1$-$C_x$ alkoxy," "$C_1$-$C_x$ alkenoxy," and "$C_1$-$C_x$ alkynoxy," groups, when x is an integer greater than 2, such "$C_1$-$C_x$ alkyl," "$C_1$-$C_x$ alkenyl," "$C_1$-$C_x$ alkynyl," "$C_1$-$C_x$ alkoxy," "$C_1$-$C_x$ alkenoxy," and "$C_1$-$C_x$ alkynoxy," groups, may optionally be replaced with a "polyfluoro $C_1$-$C_x$ alkyl," a "polyfluoro $C_1$-$C_x$ alkenyl," a "polyfluoro $C_1$-$C_x$ alkynyl," a "polyfluoro $C_1$-$C_x$ alkoxy," a "polyfluoro $C_1$-$C_x$ alkenoxy," or a "polyfluoro $C_1$-$C_x$ alkynoxy," group. As used herein, the expression "polyfluoro $C_1$-$C_x$ alkyl" refers to alkyl groups, as defined above, that comprise at least one —$CF_2$ and/or $CF_3$ group.

Unless otherwise indicated, as used herein, the term "cycloalkyl" includes non-aromatic saturated cyclic alkyl moieties wherein alkyl is as defined above. Examples of cycloalkyl groups include, but are not limited to, cyclopropyl, cyclobutyl, cyclopentyl, cyclohexyl, and cycloheptyl. "Bicycloalkyl" and "tricycloalkyl" groups are non-aromatic saturated cyclic alkyl moieties consisting of two or three rings, respectively, wherein said rings share at least one carbon atom which may contain a carbon bridge. For purposes of the present invention, and unless otherwise indicated, bicycloalkyl groups include spiro groups and fused ring groups. Examples of bicycloalkyl groups include, but are not limited to, bicyclo-[3.1.0]-hexyl, bicyclo-[2.2.1]-hept-1-yl, norbornyl, spiro[4.5]decyl, spiro[4.4]nonyl, spiro[4.3]octyl, and spiro[4.2]heptyl. An example of a tricycloalkyl group is adamantanyl. Other cycloalkyl, bicycloalkyl, and tricycloalkyl groups are known in the art, and such groups are encompassed by the definitions "cycloalkyl", "bicycloalkyl" and "tricycloalkyl" herein. "Cycloalkenyl", "bicycloalkenyl" and "tricycloalkenyl" refer, respectively, to non-aromatic cycloalkyl, bicycloalkyl and tricycloalkyl moieties, respectively, as defined above, except that they each include one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl, cyclobutenyl, and cyclohexenyl. A non-limiting example of a bicycloalkenyl group is norbornenyl. Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl and norcamphoryl. Other cycloalkenyl, bicycloalkenyl, and tricycloalkenyl groups are known in the art, and such groups are included within the definitions "cycloalkenyl", "bicycloalkenyl" and "tricycloalkenyl" herein.

Unless otherwise indicated, as used herein, the term "aryl" includes an organic radical derived from an aromatic hydrocarbon by removal of one hydrogen, such as phenyl (Ph), naphthyl, indenyl, indanyl and fluorenyl. "Aryl" encompasses fused ring groups wherein at least one ring is aromatic.

Unless otherwise indicated, as used herein, the terms "heterocyclic" and "heterocycloalkyl" refer to non-aromatic cyclic groups containing one or more heteroatoms, preferably from one to four heteroatoms, each independently selected from O, S and N. "Heterobicycloalkyl" groups are non-aromatic two-ringed cyclic groups, wherein said rings share one or two atoms, and wherein at least one of the rings contains a heteroatom (O, S, or N). Unless otherwise indicated, for purposes of the present invention, heterobicycloalkyl groups include spiro groups and fused ring groups. In one embodiment, each ring in the heterobicycloalkyl group contains up to four heteroatoms (i.e. from zero to four heteroatoms, provided that at least one ring contains at least one heteroatom). The heterocyclic groups of this invention can also include ring systems substituted with one or more oxo moieties. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro([4.5]decyl, 1,4-dioxaspiro[4.4]nonyl, 1,4-dioxaspiro[4.3]octyl, and 1,4-dioxaspiro[4.2]heptyl.

Unless otherwise indicated, as used herein, "heteroaryl" refers to aromatic groups containing one or more heteroatoms, preferably from one to four heteroatoms, selected from O, S and N. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroguinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

Unless otherwise indicated, as used herein, the term "cycloalkoxy", means "cycloalkyl-O—", wherein "cycloalkyl" is as defined above.

Unless otherwise indicated, as used herein, the term "aryloxy", means "aryl-O—", wherein "aryl" is as defined above.

Unless otherwise indicated, as used herein, the term "heterocycloalkoxy", means "heterocycloalkyl-O—", wherein "heterocycloalkyl" is as defined above.

Unless otherwise indicated, as used herein, the term "heteroaryloxy", means "heteroaryl-O—", wherein "heteroaryl" is as defined above.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

In another aspect, the present invention relates to compounds of the Formula I, wherein Z is —C(=O)CHR$^1$R$^2$, R$^2$ is —H, —OH, or OC(=O)CH$_3$.

In another aspect, the present invention relates to compounds of the Formula I, wherein Z is —C(=O)C(=O)R$^1$.

In another aspect, the present invention relates to compounds of the Formula I, wherein Z is —SO$_2$R$^1$.

In another aspect, the present invention relates to compounds of the Formula I wherein R$^1$ is selected from —C$_1$-C$_{20}$ alkyl, —C$_2$-C$_{20}$ alkenyl, —C$_2$-C$_{20}$ alkynyl, —C$_3$-C$_{20}$ cycloalkyl, (4-20 membered) heterocycloalkyl, —C$_8$-C$_{20}$ aryl and (5-20 membered) heteroaryl.

In another aspect, R$^1$ is selected from —C$_1$-C$_{10}$ alkyl, —C$_2$-C$_{10}$ alkenyl, —C$_3$-C$_{10}$ cycloalkyl, phenyl, thienyl and pyridyl, wherein R$^1$ is optionally independently substituted with from one to two substituents independently selected from —C$_1$-C$_4$ alkyl, —OCF$_3$, —CF$_3$, —C$_1$-C$_4$ alkoxy, —F, —Cl, —Br, phenyl and phenoxy, wherein R$^1$ optionally contains one or two double or triple bonds.

In another aspect, R$^1$ is —C$_3$-C$_7$ cycloalkyl, e.g., [2.2.1]-heptanyl.

In another aspect, R$^1$ is selected from phenyl and pyridyl, wherein R$^1$ is optionally independently substituted with from one to two substitutents independently selected from —F, —Cl, OCF$_3$, and —CF$_3$.

In another aspect, the present invention relates to compounds of the Formula I wherein $R^2$ is selected from —H, —OH, and —OC(=O)CH$_3$.

In another aspect, $R^2$ is selected from —H and —OH.

In another aspect, $R^2$ is selected from —OC(=O)CH$_3$.

In another aspect, the present invention relates to compounds of the Formula I wherein $R^3$ is selected from —C$_1$-C$_4$ alkyl, allyl, and —CH$_2$CH$_2$SCH$_3$.

In another aspect, the present invention relates to compounds of the Formula I wherein $R^5$ is H.

In another aspect, the present invention relates to compounds of the Formula I wherein $R^7$ is selected from —H, —C$_1$-C$_{12}$ alkyl, —C$_2$-C$_{12}$ alkenyl, —C$_1$-C$_{20}$ alkoxy, —F, —Cl, —Br, —I, —CN, —NO$_2$, —C$_3$-C$_{15}$ cycloalkyl, -(3-15 membered) heterocycloalkyl, —C$_6$-C$_{15}$ aryl, -(5-15 membered) heteroaryl, —CHO, —C(=O)(C$_1$-C$_{15}$ alkyl), —C(=O)((5-15 membered)heterocycloalkyl), —C(=O)((5-15 membered) heteroaryl), —C(=O)O(C$_1$-C$_8$ alkyl), —C(=O)N(C$_1$-C$_{10}$ alkyl)(C$_1$-C$_{10}$ alkyl), —S(O)$_n$-alkyl, —S(O)$_n$-cycloalkyl, —S(O)$_n$-(6 to 14 membered) aryl, —S(O)$_n$-(5 to 14 membered) heteroaryl, wherein said alkyl, cycloalkyl, heterocycloalkyl, aryl and heteroaryl are each optionally independently substituted with from one to three substituents independently selected from —F, —Cl, —Br, —I, —OH, —C$_1$-C$_6$ alkoxy, —C$_2$-C$_6$ alkenoxy, —C$_2$-C$_6$ alkynoxy, —NR$^9$R$^{10}$, —C(=O)R$^{11}$, —S(O)$_n$R$^{11}$, —C(=O)OR$^{12}$, —C(=O)NR$^9$R$^{10}$, —S(O)$_n$NR$^9$R$^{10}$—C$_3$-C$_{15}$ cycloalkyl, -(4-15 membered) heterocycloalkyl, —C$_6$-C$_{15}$ aryl, -(5-15 membered) heteroaryl, (5-15 membered) heterocycloalkoxy, —C$_6$-C$_{12}$ aryloxy and (6-12 membered) heteroaryloxy.

In another aspect, wherein $R^7$ is selected from —H, —C$_1$-C$_{12}$ alkyl, —C$_2$-C$_{12}$ alkenyl, —C$_2$-C$_{12}$ alkynyl, —C$_1$-C$_{20}$ alkoxy, —F, —Cl, —Br, —I, —CN, —NO$_2$, —(C$_{zero}$-C$_4$ alkylene)(C$_3$-C$_{15}$ cycloalkyl), -(3-15 membered) heterocycloalkyl, —C$_6$-C$_{15}$ aryl, -(5-15 membered) heteroaryl, —CHO, —C(=O)(C$_1$-C$_{15}$ alkyl), —C(=O)((5-15 membered) heterocycloalkyl), —C(=O)(C$_5$-C$_{15}$ aryl), —C(=O)((5-15 membered) heteroaryl), —C(=O)(C$_5$-C$_{15}$ cycloalkyl), —C(=O)O(C$_1$-C$_8$ alkyl), —C(=O)N(C$_1$-C$_{10}$ alkyl)(C$_1$-C$_{10}$ alkyl), —C(=O)N(C$_{zero}$-C$_{10}$ alkyl)(C$_6$-C$_{10}$ aryl), —C(=O)N(C$_{zero}$-C$_{10}$ alkyl)((5-10 membered) heteroaryl), —C(=O)N(C$_{zero}$-C$_{10}$ alkyl)((5-10 membered) heterocycloalkyl), —C(=O)N(C$_{zero}$-C$_{10}$ alkyl)(C$_5$-C$_{10}$ cycloalkyl), —S(O)$_n$—(C$_1$-C$_6$ alkyl), —S(O)$_n$—(C$_3$-C$_8$ cycloalkyl), —S(O)$_n$—(C$_6$-C$_{10}$ aryl), —S(O)$_n$-((5-10 membered) heteroaryl), wherein said alkyl, alkenyl, alkynyl, cycloalkyl, heterocycloalkyl, aryl and heteroaryl are each optionally independently substituted with from one to three substituents independently selected from —F, —Cl, —Br, —I, —OH, —C$_1$-C$_{10}$ alkoxy, —C$_2$-C$_{10}$ alkenoxy, —C$_2$-C$_{10}$ alkynoxy, —NR$^9$R$^{10}$, (C$_1$-C$_{11}$ alkyl)—NR$^9$R$^{10}$, —C(=O)R$^{11}$, —S(O)$_n$R$^{11}$, —C(=O)R$^{12}$, —C(=O)NR$^9$R$^{10}$, —S(O)$_n$NR$^9$R$^{10}$, —C$_3$-C$_{15}$ cycloalkyl, -(4-15 membered) heterocycloalkyl, —C$_6$-C$_{15}$ aryl, -(5-15 membered) heteroaryl, -(4-12 membered) heterocycloalkoxy, —C$_6$-C$_{12}$ aryloxy and -(6-12 membered) heteroaryloxy.

In another aspect, $R^7$ is selected from —C$_1$-C$_{12}$ alkyl, —C$_2$-C$_{12}$ alkenyl, —C$_2$-C$_{12}$ alkynyl, —(C$_{zero}$-C$_4$ alkylene)(C$_3$-C$_{15}$ cycloalkyl), and —(C$_{zero}$-C$_4$ alkylene)(4-15 membered) heterocycloalkyl, wherein said alkyl, alkenyl, cycloalkyl and heterocycloalkyl are each optionally independently substituted with from one to three substituents independently selected from —OH, —C$_1$-C$_6$ alkoxy, —C$_2$-C$_6$ alkenoxy, —C$_2$-C$_6$ alkynoxy and —NR$^9$R$^{10}$.

In another aspect, $R^7$ is selected from —C$_1$-C$_{12}$ alkyl, —C$_2$-C$_{12}$ alkenyl, —C$_3$-C$_{15}$ cycloalkyl and -(4-15 membered) heterocycloalkyl, wherein said alkyl, alkenyl, cycloalkyl and heterocycloalkyl are each optionally independently substituted with from one to three substituents independently selected from —OH, —C$_1$-C$_6$ alkoxy, —C$_2$-C$_6$ alkenoxy, —C$_2$-C$_6$ alkynoxy.

In another aspect, $R^7$ is selected from —C$_1$-C$_{12}$ alkyl, —C$_2$-C$_{12}$-alkenyl and —C$_3$-C$_{15}$ cycloalkyl, wherein said alkyl, alkenyl and cycloalkyl are each optionally independently substituted with from one to three substituents NR$^9$R$^{10}$.

In another aspect, $R^7$ is -(4-15 membered) heterocycloalkyl, wherein said heterocycloalkyl is optionally substituted with from one to three substituents independently selected from —OH, —C$_1$-C$_6$ alkyl, —C$_2$-C$_6$ alkenyl, —C$_2$-C$_6$ alkynyl, —C$_1$-C$_6$ alkoxy, —C$_2$-C$_6$ alkenoxy, —C$_2$-C$_6$ alkynoxy, —(C$_6$-C$_{10}$ aryl) and -(5-15 membered) heteroaryl.

Non-limiting examples of the compound of formula I include the following compounds:

2-[2-(3,5-Difluoro-phenyl)-acetylamino]-pentanoic acid (5-phenyl-[1,3,4]thiadiazol-2-yl)amide;

2-[2-(3,5-Difluoro-phenyl)-acetylamino]-pentanoic acid [5-(4-methoxy-phenyl)-[1,3,4]thiadiazol-2-yl]-amide;

2-[2-(3,5-Difluoro-phenyl)-acetylamino]-pentanoic acid [5-(3,4-dimethyl-benzylsulfanyl)-[1,3,4]thiadiazol-2-yl]-amide;

2-[2-(3,5-Difluoro-phenyl)-acetylamino]-pentanoic acid (5-adamantan-1-yl-[1,3,4]thiadiazol-2-yl)-amide;

2-[2-(3,5-Difluoro-phenyl)-acetylamino]-pentanoic acid [5-(4-chloro-benzyl)-[1,3,4]thiadiazol-2-yl]-amide;

2-[2-(3,5-Difluoro-phenyl)-acetylamino]-pentanoic acid [5-(2-phenyl-propylsulfanyl)-[1,3,4]thiadiazol-2-yl]-amide;

2-[2-(3,5-Difluoro-phenyl)-acetylamino]-pentanoic acid [5-(3-trifluoromethyl-benzylsulfanyl)-thiazol-2-yl]-amide;

2-[2-(3,5-Difluoro-phenyl)-acetylamino]-pentanoic acid [5-(3-methoxy-benzylsulfanyl)-thiazol-2-yl]-amide;

2-[2-(3,5-Difluoro-phenyl)-acetylamino]-pentanoic acid [5-(2-fluoro-benzylsulfanyl)-thiazol-2-yl]-amide;

2-[2-(3,5-Difluoro-phenyl)-acetylamino]-pentanoic acid (5-propylsulfamoyl-[1,3,4]thiadiazol-2-yl)amide;

2-[2-(3,5-Difluoro-phenyl)-acetylamino]-pentanoic acid {5-[2-(3-trifluoromethyl-phenoxy)-ethylsulfanyl]-[1,3,4]thiadiazol-2-yl}-amide;

2-[2-(3,5-Difluoro-phenyl)-acetylamino]-pentanoic acid [5-(3,4-dichloro-benzylsulfanyl)-[1,3,4]thiadiazol-2-yl]-amide;

2-[2-(3,5-Difluoro-phenyl)-acetylamino]-pentanoic acid (5-dipropylsulfamoyl-[1,3,4]thiadiazol-2-yl)-amide;

2-[2-(3,5-Difluoro-phenyl)-acetylamino]-pentanoic acid (5-benzylsulfanyl-[1,3,4]thiadiazol-2-yl)-amide;

2-[2-(3,5-Difluoro-phenyl)-acetylamino]-pentanoic acid {5-[1-(2,4-dichloro-phenoxy)-ethyl]-[1,3,4]thiadiazol-2-yl}-amide;

2-[2-(3,5-Difluoro-phenyl)-acetylamino]-pentanoic acid [5-(4-phenoxy-butylsulfanyl)-thiazol-2-yl]-amide;

2-[2-(3,5-Difluoro-phenyl)-acetylamino]-pentanoic acid {5-[2-(4-bromo-phenoxy)-ethylsulfanyl]-thiazol-2-yl}amide;

2-[2-(3,5-Difluoro-phenyl)-acetylamino]-pentanoic acid (5-diethylsulfamoyl-[1,3,4]thiadiazol-2-yl)-amide;

2-[2-(3,5-Difluoro-phenyl)-acetylamino]-pentanoic acid (5-ethylsulfamoyl-[1,3,4]thiadiazol-2-yl)-amide;

2-[2-(3,5-Difluoro-phenyl)-acetylamino]-pentanoic acid (5-phenethylsulfanyl-[1,3,4]thiadiazol-2-yl)-amide;

2-[2-(3,5-Difluoro-phenyl)-acetylamino]-pentanoic acid (5-tert-butyl-[1,3,4]thiadiazol-2-yl)-amide;

2-(2-Hydroxy-2-phenyl-acetylamino)-pentanoic acid (5-tert-butyl-[1,3,4]thiadiazol-2-yl)-amide;

2-(2-Hydroxy-3,3-dimethyl-butyrylamino)-pentanoic acid (5-tert-butyl-[1,3,4]thiadiazol-2-yl)-amide;

2-(2-Hydroxy-3-methyl-butyrylamino)-pentanoic acid (5-tert-butyl-[1,3,4]thiadiazol-2-yl)-amide;

2-[2-(3,5-Difluoro-phenyl)-2-(S)-2-hydroxy-acetylamino]-pentanoic acid (5-tert-butyl-[1,3,4]thiadiazol-2-yl)-amide;

2-[2-(3,5-Difluoro-phenyl)-2-(S)-2-hydroxy-acetylamino]-pentanoic acid (5-tert-butyl-[1,3,4]thiadiazol-2-yl)-amide;

2-[2-(3,5-Difluoro-phenyl)-2-(S)-hydroxy-acetylamino]-pentanoic acid (5-tert-butyl-[1,3,4]thiadiazol-2-yl)-amide;

2-[2-(5-Bromo-pyridin-3-yl)-acetylamino]-pentanoic acid (5-tert-butyl-[1,3,4]thiadiazol-2-yl)-amide;

2-(2-Bicyclo[2.2.1]hept-2-yl-acetylamino)-pentanoic acid (5-tert-butyl-[1,3,4]thiadiazol-2-yl)-amide;

2-[2-(3,5-Difluoro-phenyl)-acetylamino]-pentanoic acid (5-ethyl-[1,3,4]thiadiazol-2-yl)-amide;

2-(2-Hydroxy-3-methyl-butyrylamino)-pentanoic acid (5-ethyl-[1,3,4]thiadiazol-2-yl)-amide;

2-[2-(5-Bromo-pyridin-3-yl)-acetylamino]-pentanoic acid (5-ethyl-[1,3,4]thiadiazol-2-yl)-amide;

2-(2-Bicyclo[2.2.1]hept-2-yl-acetylamino)-pentanoic acid (5-ethyl-[1,3,4]thiadiazol-2-yl)-amide;

2-[2-(3,5-Difluoro-phenyl)-acetylamino]-pentanoic acid (5-methyl-[1,3,4]thiadiazol-2-yl)-amide;

2-(2-(S)-2-Hydroxy-2-phenyl-acetylamino)-pentanoic acid (5-methyl-[1,3,4]thiadiazol-2-yl)-amide;

2-(2-(R)-2-Hydroxy-2-phenyl-acetylamino)-pentanoic acid (5-methyl-[1,3,4]thiadiazol-2-yl)-amide;

Hydroxy-phenyl-acetic acid [1-(5-methyl-[1,3,4]thiadiazol-2-ylcarbamoyl)-butylcarbamoyl]-phenyl-methyl ester;

2-(2-Hydroxy-3,3-dimethyl-butyrylamino)-pentanoic acid (5-methyl-[1,3,4]thiadiazol-2-yl)-amide;

2-(2-Hydroxy-3-methyl-butyrylamino)-pentanoic acid (5-methyl-[1,3,4]thiadiazol-2-yl)-amide;

2-[2-(3,5-Difluoro-phenyl)-2-(S)-2-hydroxy-acetylamino]-pentanoic acid (5-methyl-[1,3,4]thiadiazol-2-yl)-amide;

2-[2-(3,5-Difluoro-phenyl-2-(R)-2-hydroxy-acetylamino]-pentanoic acid (5-methyl-[1,3,4]thiadiazol-2-yl)-amide;

2-[2-(3,5-Difluoro-phenyl)-acetylamino]-pentanoic acid (5-cyclopropyl-[1,3,4]thiadiazol-2-yl)-amide;

2-[2-(3,5-Difluoro-phenyl)-acetylamino]-pentanoic acid (5-trifluoromethyl-[1,3,4]thiadiazol-2-yl)-amide;

2-[2-(3,5-Difluoro-phenyl)-acetylamino]-pentanoic acid (5-formyl-[1,3,4]thiadiazol-2-yl)-amide;

2-[2-(2,5-Difluoro-phenyl)-acetylamino]-pentanoic acid (5-tert-butyl-[1,3,4]thiadiazol-2-yl)-amide;

2-[2-(3,5-Difluoro-phenyl)-acetylamino]-pentanoic acid [5-(1-ethyl-propyl)-[1,3,4]thiadiazol-2-yl]-amide;

2-[2-(3,5-Difluoro-phenyl)-acetylamino]-pentanoic acid [5-(2,4,4-trimethyl-pentyl)-[1,3,4]thiadiazol-2-yl]-amide;

2-[2-(3,5-Difluoro-phenyl)-acetylamino]-pentanoic acid [5-(1-ethyl-pentyl)-[1,3,4]thiadiazol-2-yl]-amide;

2-(2-(S)-2-Hydroxy-3,3-dimethyl-butyrylamino)-pentanoic acid [5-(1-ethyl-pentyl)-[1,3,4]thiadiazol-2-yl]-amide;

2-(2-(R)-2-Hydroxy-3,3-dimethyl-butyrylamino)-pentanoic acid [5-(1-ethyl-pentyl)-[1,3,4]thiadiazol-2-yl]-amide;

2-(2-(S)-2-Hydroxy-3,3-dimethyl-butyrylamino)-pentanoic acid [5-(1-ethyl-propyl)-[1,3,4]thiadiazol-2-yl]-amide;

2-(2-(R)-2-Hydroxy-3,3-dimethyl-butyrylamino)-pentanoic acid [5-(1-ethyl-propyl)-[1,3,4]thiadiazol-2-yl]-amide;

2-(2-(S)-2-Hydroxy-2-phenyl-acetylamino)-pentanoic acid [5-(1 ethyl-propyl)-[1,3,4]thiadiazol-2-yl]-amide;

2-(2-(R)-2-Hydroxy-2-phenyl-acetylamino)-pentanoic acid [5-(1-ethyl-propyl)-[1,3,4]thiadiazol-2-yl]-amide;

2-[2-(3,5-Difluoro-phenyl)-acetylamino]-pentanoic acid [5-(1,1-dimethyl-but-3-enyl)-[1,3,4]thiadiazol-2-yl]-amide;

2-(2-(S)-Hydroxy-2-phenyl-acetylamino)-pentanoic acid [5-(1-ethyl-pentyl)-[1,3,4]thiadiazol-2-yl]-amide;

2-(2-(R)-Hydroxy-2-phenyl-acetylamino)-pentanoic acid [5-(1-ethyl-pentyl)-[1,3,4]thiadiazol-2-yl]-amide;

2-[2-(3,5-Difluoro-phenyl)-acetylamino]-pentanoic acid [5-(1,1-dimethyl-3-oxo-propyl)-[1,3,4]thiadiazol-2-yl]-amide;

2-[2-(3,5-Difluoro-phenyl)-acetylamino]-pentanoic acid [5-(3-isopropylamino-1,1-dimethyl-propyl)-[1,3,4]thiadiazol-2-yl]-amide;

2-[2-(3,5-Difluoro-phenyl)-acetylamino]-pentanoic acid [5-(1,1-dimethyl-butyl)-[1,3,4]thiadiazol-2-yl]-amide;

2-(2-Hydroxy-2-phenyl-acetylamino)-pentanoic acid [5-(1,1-dimethyl-butyl)-[1,3,4]thiadiazol-2-yl]-amide;

2-(2-Hydroxy-3,3-dimethyl-butyrylamino)-pentanoic acid [5-(1,1-dimethyl-butyl)-[1,3,4]thiadiazol-2-yl]-amide;

2-(2-Hydroxy-3-methyl-butyrylamino)-pentanoic acid [5-(1,1-dimethyl-butyl)-[1,3,4]thiadiazol-2-yl]-amide;

2-[2-(S)-2-(3,5-Difluoro-phenyl)-2-hydroxy-acetylamino]-pentanoic acid [5-(1,1-dimethyl-butyl)-[1,3,4]thiadiazol-2-yl]-amide;

2-[2-(R)-2-(3,5-Difluoro-phenyl)-2-hydroxy-acetylamino]-pentanoic acid [5-(1,1-dimethyl-butyl)-[1,3,4]thiadiazol-2-yl]-amide;

2-[2-(5-Bromo-pyridin-3-yl)-acetylamino]-pentanoic acid [5-(1,1-dimethyl-butyl)-[1,3,4]thiadiazol-2-yl]-amide;

2-[2-(3-Trifluoromethoxy-phenyl)-acetylamino]-pentanoic acid [5-(1,1-dimethyl-butyl)-[1,3,4]thiadiazol-2-yl]-amide;

3-(5-{2-[2-(3,5-Difluoro-phenyl)-acetylamino]-pentanoylamino}-[1,3,4]thiadiazol-2-yl)-3-methyl-butyric acid;

2-[2-(3,5-Difluoro-phenyl)-acetylamino]-pentanoic acid [5-(1,1-dimethyl-2-oxiranyl-ethyl)-[1,3,4]thiadiazol-2-yl]-amide;

2-[2-(3,5-Difluoro-phenyl)-acetylamino]-pentanoic acid [5-(1,1-dimethyl-but-3-enyl)-3-oxy-[1,3,4]thiadiazol-2-yl]-amide;

2-[2-(3,5-Difluoro-phenyl)-acetylamino]-pentanoic acid {5-[1,1-dimethyl-3-(2,2,2-trifluoro-ethylamino)-propyl]-[1,3,4]thiadiazol-2-yl}-amide;

2-[2-(3,5-Difluoro-phenyl)-acetylamino]-pentanoic acid [5-(1-methyl-but-3-enyl)-[1,3,4]thiadiazol-2-yl]-amide;

2-[2-(3,5-Difluoro-phenyl)-acetylamino]-N-[5-(1-methyl-but-3-enyl)-[1,3,4]thiadiazol-2-yl]-butyramide;

2-[2-(3,5-Difluoro-phenyl)-acetylamino]-pentanoic acid [5-(1-methyl-butyl)-[1,3,4]thiadiazol-2-yl]-amide;

2-[2-(3,5-Difluoro-phenyl)-acetylamino]-N-[5-(1-methyl-butyl-)[1,3,4]thiadiazol-2-yl]-butyramide;

2-[2-(3,5-Difluoro-phenyl)-acetylamino]-N-[5-(1,1-dimethyl-but-3-enyl)-[1,3,4]thiadiazol-2-yl]-butyramide;

2-[2-(3,5-Difluoro-phenyl)-acetylamino]-pentanoic acid [5-(1-methyl-3-oxo-propyl)-[1,3,4]thiadiazol-2-yl]-amide;

2-[2-(3,5-Difluoro-phenyl)-acetylamino]-N-[5-(1-methyl-3-oxo-propyl)-[1,3,4]thiadiazol-2-yl]-butyramide;

2-[2-(3,5-Difluoro-phenyl)-acetylamino]-pentanoic acid [5-(3-isopropylamino-1-methyl-propyl)-[1,3,4]thiadiazol-2-yl]-amide;

2-[2-(3,5-Difluoro-phenyl)-acetylamino]-pentanoic acid [5-(3,3-dimethoxy-1,1-dimethyl-propyl)-[1,3,4]thiadiazol-2-yl]-amide;

2-(2-Hydroxy-3,3-dimethyl-butyrylamino)-pentanoic acid [5-(1,1-dimethyl-but-3-enyl)-[1,3,4]thiadiazol-2-yl]-amide;

2-[2-(3,5-Difluoro-phenyl)-acetylamino]-N-[5-(3-ethylamino-1-methyl-propyl)-[1,3,4]thiadiazol-2-yl]-butyramide;

2-[2-(3,5-Difluoro-phenyl)-acetylamino]-N-[5-(3-isopropylamino-1-methyl-propyl)-[1,3,4]thiadiazol-2-yl]-butyramide;

2-[2-(3,5-Difluoro-phenyl)-acetylamino]-N-[5-(1,1-dimethyl-3-oxo-propyl)-[1,3,4]thiadiazol-2-yl]-butyramide;

2-[2-(3,5-Difluoro-phenyl)-acetylamino]-N-[5-(3-hydroxy-1,1-dimethyl-propyl)-[1,3,4]thiadiazol-2-yl]-butyramide;

2-[2-(3,5-Difluoro-phenyl)-acetylamino]-N-[5-(3-isopropylamino-1,1-dimethyl-propyl)-[1,3,4]thiadiazol-2-yl]-butyramide;

2-[2-(3,5-Difluoro-phenyl)-acetylamino]-pentanoic acid [5-(3-ethylamino-1,1-dimethyl-propyl)-[1,3,4]thiadiazol-2-yl]-amide;

2-(2-Hydroxy-2-phenyl-acetylamino)-pentanoic acid [5-(1,1-dimethyl-but-3-enyl)-[1,3,4]thiadiazol-2-yl]-amide;

2-(2-Hydroxy-3-methyl-butyrylamino)-pentanoic acid [5-(1,1-dimethyl-but-3-enyl)-[1,3,4]thiadiazol-2-yl]-amide;

2-[2-(3,5-Difluoro-phenyl)-2-(R)-2-hydroxy-acetylamino]-pentanoic acid [5-(1,1-dimethyl-but-3-enyl)-[1,3,4]thiadiazol-2-yl]-amide;

2-[2-(3,5-Difluoro-phenyl)-2-(S)-2-hydroxy-acetylamino]-pentanoic acid [5-(1,1-dimethyl-but-3-enyl)-[1,3,4]thiadiazol-2-yl]-amide;

2-[2-(3,5-Difluoro-phenyl)-acetylamino]-pentanoic acid [5-(3-dimethylamino-1,1-dimethyl-propyl)-[1,3,4]thiadiazol-2-yl]-amide;

2-[2-(3,5-Difluoro-phenyl)-acetylamino]-pentanoic acid [5-(1,1-dimethyl-3-propylamino-propyl)-[1,3,4]thiadiazol-2-yl]-amide;

2-[2-(3,5-Difluoro-phenyl)-acetylamino]-pentanoic acid {5-[3-(2-hydroxy-ethylamino)-1,1-dimethyl-propyl]-[1,3,4]thiadiazol-2-yl}-amide;

2-[2-(3,5-Difluoro-phenyl)-acetylamino]-pentanoic acid [5-(3-tert-butylamino-1,1-dimethyl-propyl)-[1,3,4]thiadiazol-2-yl]-amide;

2-[2-(3,5-Difluoro-phenyl)-acetylamino]-pentanoic acid [5-(3-cyclopropylamino-1,1-dimethyl-propyl)-[1,3,4]thiadiazol-2-yl]-amide;

2-[2-(3,5-Difluoro-phenyl)-acetylamino]-pentanoic acid [5-(1,1-dimethyl-3-pyrrolidin-1-yl-propyl)-[1,3,4]thiadiazol-2-yl]-amide;

2-[2-(3,5-Difluoro-phenyl)-acetylamino]-pentanoic acid [5-(1,1-dimethyl-3-morpholin-4-yl-propyl)-[1,3,4]thiadiazol-2-yl]-amide;

2-[2-(3,5-Difluoro-phenyl)-acetylamino]-pentanoic acid {5-[3-(1-ethyl-propylamino)-1,1-dimethyl-propyl]-[1,3,4]thiadiazol-2-yl}-amide;

2-[2-(3,5-Difluoro-phenyl)-2-hydroxy-acetylamino]-pentanoic acid [5-(3-cyclopropylamino-1,1-dimethyl-propyl)-[1,3,4]thiadiazol-2-yl]-amide;

2-[2-(3,5-Difluoro-phenyl)-acetylamino]-pentanoic acid [5-(3-hydroxy-1,1-dimethyl-propyl)-[1,3,4]thiadiazol-2-yl]-amide-2-[2-(3,5-Difluoro-phenyl)-acetylamino]-pentanoic acid (5-{3-[formyl-(2,2,2-trifluoro-ethyl)amino]-1,1-dimethyl-propyl}-[1,3,4]thiadiazol-2-yl)-amide 2-[2-(3,5-Difluoro-phenyl)-2-hydroxy-acetylamino]-pentanoic acid (5-{3-[formyl-(2,2,2-trifluoro-ethyl)amino]-1,1-dimethyl-propyl}-[1,3,4]thiadiazol-2-yl)-amide;

2-[2-(3,5-Difluoro-phenyl)-2-hydroxy-acetylamino]-pentanoic acid [5-(1,1-dimethyl-3-oxo-propyl)-[1,3,4]thiadiazol-2-yl]-amide;

2-(2-Hydroxy-3,3-dimethyl-butyrylamino)-pentanoic acid (5-cyclopropyl-[1,3,4]thiadiazol-2-yl)-amide;

2-(2-Hydroxy-3-methyl-butyrylamino)-pentanoic acid (5-cyclopropyl-[1,3,4]thiadiazol-2-yl)-amide;

2-[2-(3,5-Difluoro-phenyl)-2-hydroxy-acetylamino]-pentanoic acid (5-cyclopropyl-[1,3,4]thiadiazol-2-yl)-amide;

2-(2-Hydroxy-2-phenyl-acetylamino)-pentanoic acid (5-cyclopropyl-[1,3,4]thiadiazol-2-yl)-amide;

2-[2-(3,5-Difluoro-phenyl)-acetylamino]-pentanoic acid [5-(2-chloro-1,1-dimethyl-ethyl)-[1,3,4]thiadiazol-2-yl]-amide;

2-[2-(3,5-Difluoro-phenyl)-acetylamino]-pentanoic acid [5-(2-hydroxy-1,1-dimethyl-ethyl)-[1,3,4]thiadiazol-2-yl]-amide;

2-(5-{2-[2-(3,5-Difluoro-phenyl)-acetylamino]-pentanoylamino}-[1,3,4]thiadiazol-2-ylsulfanyl)-2-methyl-propionic acid ethyl ester;

2-[2-(3,5-Difluoro-phenyl)-acetylamino]-pentanoic acid {5-[(isopropyl-phenyl-carbamoyl)-methylsulfanyl]-[1,3,4]thiadiazol-2-yl}-amide;

2-[2-(3,5-Difluoro-phenyl)-acetylamino]-pentanoic acid [5-(3-fluoro-benzylsulfanyl)-[1,3,4]thiadiazol-2-yl]-amide;

2-[2-(3,5-Difluoro-phenyl)-acetylamino]-pentanoic acid [5-(4-trifluoromethyl-pyrimidin-2-ylsulfanyl)-[1,3,4]thiadiazol-2-yl]-amide;

2-[2-(3,5-Difluoro-phenyl)-acetylamino]-pentanoic acid [5-(1-methyl-allyl)-[1,3,4]thiadiazol-2-yl]-amide;

2-[2-(3,5-Difluoro-phenyl)-acetylamino]-pentanoic acid [5-(1-methyl-propenyl)-[1,3,4]thiadiazol-2-yl]-amide;

2-[2-(3,5-Difluoro-phenyl)-acetylamino]-pentanoic acid [5-acetyl-[1,3,4]thiadiazol-2-yl]-amide;

2-[2-(3,5-Difluoro-phenyl)-acetylamino]-pentanoic acid {5-[1-(3-methyl-butylamino)-ethyl]-[1,3,4]thiadiazol-2-yl}-amide;

2-[2-(3,5-Difluoro-phenyl)-acetylamino]-pentanoic acid [5-(1-butylamino-ethyl)-[1,3,4]thiadiazol-2-yl]-amide;

2-[2-(3,5-Difluoro-phenyl)-acetylamino]-pentanoic acid {5-[1-(3,3-dimethyl-butylamino)-ethyl]-[1,3,4]thiadiazol-2-yl}amide;

2-[2-(3,5-Difluoro-phenyl)-acetylamino]-pentanoic acid [5-(1-cyclopropylamino-ethyl)-[1,3,4]thiadiazol-2-yl]-amide;

2-[2-(3,5-Difluoro-phenyl)-acetylamino]-pentanoic acid [5-(1,1-dimethyl-2-oxo-ethyl)-[1,3,4]thiadiazol-2-yl]-amide;

2-[2-(3,5-Difluoro-phenyl)-acetylamino]-pentanoic acid {5-[1-(4-methyl-piperazin-1-yl)-ethyl]-[1,3,4]thiadiazol-2-yl}-amide;

2-[2-(3,5-Difluoro-phenyl)-acetylamino]-pentanoic acid {5-[1-(4-chloro-benzylamino)-ethyl]-[1,3,4]thiadiazol-2-yl}-amide;

2-[2-(3,5-Difluoro-phenyl)-acetylamino]-pentanoic acid [5-(1-hydroxy-ethyl)-[1,3,4]thiadiazol-2-yl]-amide;

2-[2-(3,5-Difluoro-phenyl)-acetylamino]-pentanoic acid {5-[1-(3-chloro-benzylamino)-ethyl]-[1,3,4]thiadiazol-2-yl}-amide;

2-[2-(3,5-Difluoro-phenyl)-acetylamino]-pentanoic acid [5-(2-benzyloxy-1,1-dimethyl-ethyl)-[1,3,4]thiadiazol-2-yl]-amide;

2-[2-(3,5-Difluoro-phenyl)-acetylamino]-N-(5-ethylsulfanyl-[1,3,4]thiadiazol-2-yl)-butyramide;

2-[2-(3,5-Difluoro-phenyl)-acetylamino]-N-[5-(2-dimethylamino-ethylsulfanyl)-[1,3,4]thiadiazol-2-yl]-butyramide;

2-[2-(3,5-Difluoro-phenyl)-acetylamino]-N-(5-ethoxymethyl-[1,3,4]thiadiazol-2-yl)-butyramide;

2-[2-(3,5-Difluoro-phenyl)-acetylamino]-N-(5-dimethylamino-[1,3,4]thiadiazol-2-yl)-butyramide;

2-[2-(3,5-Difluoro-phenyl)-acetylamino]-N-(5-isobutyl-[1,3,4]thiadiazol-2-yl)-butyramide;

2-[2-(3,5-Difluoro-phenyl)-acetylamino]-N-(5-phenyl-[1,3,4]thiadiazol-2-yl)-butyramide;

2-[2-(3,5-Difluoro-phenyl)-acetylamino]-N-(5-isopropyl-[1,3,4]thiadiazol-2-yl)-butyramide;

N-(5-Benzyl-[1,3,4]thiadiazol-2-yl)-2-[2-(3,5-difluoro-phenyl)-acetylamino]-butyramide;

2-[2-(3,5-Difluoro-phenyl)-acetylamino]-N-(5-phenoxymethyl-[1,3,4]thiadiazol-2-yl)-butyramide;

N-[5-(3-Chloro-phenyl)-[1,3,4]thiadiazol-2-yl]-2-[2-(3,5-difluoro-phenyl)-acetylamino]-butyramide;

N-(5-Cyclobutyl-[1,3,4]thiadiazol-2-yl)-2-[2-(3,5-difluoro-phenyl)-acetylamino]-butyramide;

2-[2-(3,5-Difluoro-phenyl)-acetylamino]-N-[5-(5-methyl-3-phenyl-isoxazol-4-yl)-[1,3,4]thiadiazol-2-yl]-butyramide;

2-[2-(3,5-Difluoro-phenyl)-acetylamino]-N-(5-methoxymethyl-[1,3,4]thiadiazol-2-yl)-butyramide;

2-[2-(3,5-Difluoro-phenyl)-acetylamino]-N-(5-isopropylsulfanyl-[1,3,4]thiadiazol-2-yl)-butyramide;

2-[2-(3-Phenoxy-phenyl)-acetylamino]-pentanoic acid (5-cyclohexyl-[1,3,4]thiadiazol-2-yl)-amide;

2-[2-(3-Phenoxy-phenyl)-acetylamino]-pentanoic acid (5-methylsulfamoyl-[1,3,4]thiadiazol-2-yl)-amide;

2-(5-{2-[2-(3-Phenoxy-phenyl)-acetylamino]-pentanoylamino}-[1,3,4]thiadiazol-2-ylsulfanyl)-propionic acid ethyl ester;

2-[2-(3-Phenoxy-phenyl)-acetylamino]-pentanoic acid (5-phenethyl-[1,3,4]thiadiazol-2-yl)-amide;

2-[2-(3-Phenoxy-phenyl)-acetylamino]-pentanoic acid [5-(1-phenoxy-ethyl)-[1,3,4]thiadiazol-2-yl]-amide;

2-[2-(3,5-Difluoro-phenyl)-acetylamino]-N-[3-(toluene-4-sulfonylamino)-[1,2,4]thiadiazol-5-yl]-butyramide;

2-[2-(3,5-Difluoro-phenyl)-acetylamino]-pentanoic acid (3-ethylsulfanyl-[1,2,4]thiadiazol-5-yl)-amide;

2-[2-(3,5-Difluoro-phenyl)-acetylamino]-pentanoic acid [5-(1,1-dimethyl-2-morpholin-4-yl-ethyl)-[1,3,4]thiadiazol-2-yl]-amide;

2-[2-(3,5-Difluoro-phenyl)-acetylamino]-pentanoic acid [5-(1,1-dimethyl-2-pyrrolidin-1-yl-ethyl)-[1,3,4]thiadiazol-2-yl]-amide;

2-[2-(3,5-Difluoro-phenyl)-acetylamino]-pentanoic acid (3-methanesulfonyl-[1,2,4]thiadiazol-5-yl)-amide; and 2-[2-(3,5-Difluoro-phenyl)-acetylamino]-pentanoic acid [3-(4-nitro-benzenesulfonylamino)-[1,2,4]thiadiazol-5-yl]-amide.

Compounds of the Formula I of this invention, and their pharmaceutically acceptable salts, have useful pharmaceutical and medicinal properties. The compounds of Formula I, and their pharmaceutically acceptable salts inhibit the production of Aβ-peptide (thus, gamma-secretase activity) in mammals, including humans. Compounds of the Formula I, and their pharmaceutically acceptable salts, are therefore able to function as therapeutic agents in the treatment of the neurodegenerative and/or neurological disorders and diseases enumerated below, for example Alzheimer's disease, in an afflicted mammal, including a human.

The present invention also relates to a pharmaceutical composition for inhibiting or modulating Aβ-peptide production in a mammal, including a human, comprising an amount of a compound of the Formula I, or a pharmaceutically acceptable salt thereof, that is effective in inhibiting Aβ-production, and a pharmaceutically acceptable carrier.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or condition selected from the group consisting of Alzheimer's disease and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or a condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a pharmaceutical composition for treating a disease or a condition selected from the group consisting of Alzheimers disease and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a method of inhibiting Aβ-peptide production in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Aizheimer's disease and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising administering to said mammal an amount of a compound of the Formula I, or a pharmaceutically acceptable salt thereof, that is effective in treating such condition.

The present invention also relates to a method of treating a disease or condition selected from Alzheimer's disease and Down's Syndrome in a mammal, including a human, comprising administering to said mammal an amount of a compound of the Formula I, or a pharmaceutically acceptable salt thereof, that is effective in treating such condition.

The present invention also relates to a pharmaceutical composition for treating a disease or condition associated with Aβ-peptide production in a mammal, including a human, comprising (a) a compound of the Formula I, or a pharmaceutically acceptable salt thereof; (b) a memory enhancement agent, antidepressant, anxiolytic, antipsychotic agent, sleep disorder agent, anti-inflammatory agent, anti-oxidant agent, cholesterol modulating agent or anti-hypertensive agent; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome, in a mammal, including a human, comprising (a) a compound of the Formula I, or a pharmaceutically acceptable salt thereof; (b) a memory enhancement agent, antidepressant, anxiolytic, antipsychotic agent, sleep disorder agent, anti-inflammatory agent, anti-oxidant agent, cholesterol modulating agent or anti-hypertensive agent; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease and Down's Syndrome, in a mammal, including a human, comprising (a) a compound of the Formula I, or a pharmaceutically acceptable salt thereof; (b) a memory enhancement agent, antidepressant, anxiolytic, antipsychotic agent, sleep disorder agent, anti-inflammatory agent, anti-oxidant agent, cholesterol modulating agent or anti-hypertensive agent; and (c) a pharmaceutically acceptable carrier; wherein the active agents "a" and "b" above are present in amounts that render the composition effective in treating such disease or condition.

The present invention also relates to a method of treating a disease or condition associated with Aβ-peptide production in a mammal, including a human, comprising administering to said mammal (a) a compound of the Formula I, or a pharmaceutically acceptable salt thereof; and (b) a memory enhancement agent, antidepressant, anxiolytic, antipsychotic agent, sleep disorder agent, anti-inflammatory agent, anti-oxidant agent, cholesterol modulating agent or anti-hypertensive agent; wherein the active agents "a" and "b" above are present in amounts that render the composition effective in treating such disease or condition.

The present invention also relates to a method of treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome, in a mammal, including a human, comprising administering to said mammal (a) a compound of the Formula I, or a pharmaceutically acceptable salt thereof; and (b) a memory enhancement agent, antidepressant, anxi-olytic, antipsychotic agent, sleep disorder agent, anti-inflammatory agent, anti-oxidant agent, cholesterol modulating agent or anti-hypertensive agent; wherein the active agents "a" and "b" above are present in amounts that render the composition effective in treating such disease or condition.

The present invention also relates to a method of treating a disease or condition selected from the group consisting of Alzheimer's disease and Down's Syndrome, in a mammal, including a human, comprising administering to said mammal (a) a compound of the Formula I, or a pharmaceutically acceptable salt thereof; and (b) a memory enhancement agent, antidepressant, anxiolytic, antipsychotic agent, sleep disorder agent, anti-inflammatory agent, anti-oxidant agent, cholesterol modulating agent or anti-hypertensive agent; wherein the active agents "a" and "b" above are present in amounts that render the composition effective in treating such disease or condition.

Compounds of the Formula I may be used alone or used as a combination with any other drug, including, but not limited to, any memory enhancement agent, e.g., Aricept™, antidepressant agent, e.g., Zolof™, anxiolytic, antipsychotic agent, e.g., Geodon™, sleep disorder agent, anti-inflammatory agent, e.g., Celebrex™, Bextrar™, etc., anti-oxidant agent, cholesterol modulating agent (for example, an agent that lowers LDL or increases HDL), e.g., Lipitor™, or anti-hypertension agent. Accordingly, this invention also provides a pharmaceutical composition for treatment of a mammal, including a human, in need thereof comprising an effective amount of a compound of the Formula I and an effective amount of another drug, for example a memory enhancement agent, e.g., Aricept™, antidepressant agent, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, or anti-hypertension agent, and a pharmaceutically acceptable carrier. This invention also provides a method for treating dementia, for example Alzheimer's disease, in a mammal, including in a human, comprising administering to the mammal an effective amount of a compound of the Formula I and an effective amount of another drug, for example a memory enhancement agent, e.g., Aricept™, antidepressant agent, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, or anti-hypertension agent.

Compounds of the Formula I, or any of the combinations described in the immediately preceding paragraph, may optionally be used in conjunction with a know P-glycoprotein inhibitor, such as verapamil.

References herein to diseases and conditions "associated with Aβ-peptide production" relate to diseases or conditions that are caused, at least in part, by Aβ-peptide and/or the production thereof. Thus, Aβ-peptide is a contributing factor, but not necessarily the only contributing factor, to "a disease or condition associated with Aβ-peptide production."

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

DETAILED DESCRIPTION OF THE INVENTION

Compounds of the Formula I, and their pharmaceutically acceptable salts, may be prepared as described in the following reaction Schemes and discussion. Unless otherwise indicated, as referred to in the reaction schemes and discussion that follow, $R^1$, $R^{1a}$, $R^{1b}$, $R^2$, $R^3$, $R^4$, $R^5$, $R^6$, $R^7$, $R^8$, $R^9$, $R^{10}$, $R^{11}$, $R^{12}$, Z, and n are as defined above.

The compounds of Formula I may have asymmetric carbon atoms and may therefore exist as racemic mixtures, diastereoisomers, geometric isomers, or as individual optical isomers.

Separation of a mixture of isomers of compounds of Formula I into single isomers may be accomplished according to conventional methods known in the art.

The compounds of the Formula I may be prepared by the methods described below, together with synthetic methods known in the art of organic chemistry, or modifications and derivatizations that are familiar to those of ordinary skill in the art. Preferred methods include, but are not limited to, those described below.

The reactions described below are performed in solvents that are appropriate to the reagents and materials employed and that are suitable for use in the reactions described. In the description of the synthetic methods described below, it is also to be understood that all reaction conditions, whether actual or proposed, including choice of solvent, reaction temperature, reaction duration time, reaction pressure, and other reaction conditions (such as anhydrous conditions, under argon, under nitrogen, etc.), and work up procedures, are those conditions that are standard for that reaction, as would be readily recognized by one of skill in the art. Alternate methods may also be used.

Scheme I

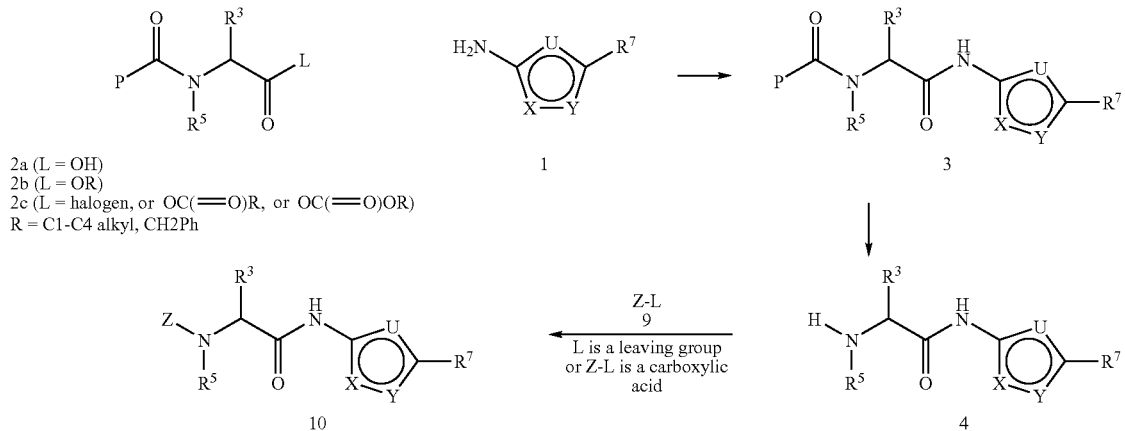

Scheme I refers to a method of preparation of compounds of the Formula I, 10. An amino-thiadiazole 1 is coupled with a nitrogen-protected amino acid 2a-c using conventional coupling reagents and procedures. The nitrogen protecting group may be a carbamate-type such as butoxycarbonyl ("BOC", P═O-tert-butyl) or benzyloxycarbonyl ("CBZ", P═O-benzyl) that is prepared with either di-tert-butyl dicarbonate (Aldrich Chemical Company, Milwaukee Wis.), or benzyl chloroformate (Aldrich) in the presence of either an inorganic or organic base (e.g., sodium carbonate or triethylamine) at 0 to 30° C. in an organic solvent (e.g., methylene chloride) or in a mixture of water and an organic solvent (e.g., ethyl acetate) (see, Muller, *Methoden Der Organischen Chemie.* "Vierte Auglage—Synthesis von Peptiden I"-Houben Weyl—Georg-Thieme Verlag Stuttgart, 1974, Band XV/1).

The amino-thiadiazoles 1 starting reagents may be prepared according to the procedure similar to the known in literature (references Acta Universitatis Palackianae Olomucensis, Facultas Rerum Naturalium, Chemica (2001); Journal of Medicinal Chemistry (2003), 46(3), 427-440. European Journal of Medicinal Chemistry (2002), 37(8), 689-697. Phosphorus, Sulfur and Silicon and the Related Elements (2002), 177(4), 863-875. Chemistry of Heterocyclic Compounds (New York, N.Y., United States)(Translation of Khimiya Geterotsiklicheskikh Soedinenii) (2001), 37(9), 1102-1106. Journal of the Institution of Chemists (India) (2001), 73(3), 108-110. Russian Journal of General Chemistry (Translation of Zhurnal Obshchei Khimii) (2000), 70(11), 1801-1803. Indian Journal of Chemistry, Section B: Organic Chemistry Including Medicinal Chemistry (1989), 28B(1), 78-80. Indian Journal of Chemistry, Section B: Organic Chemistry Including Medicinal Chemistry (1981), 20B(6), 518-20. Khimiya Geterotsiklicheskikh Soedinenii, (10), 1416-19; 1986. Journal of the Institution of Chemists (India), 61(2), 54-6; 1989 Journal of the Institution of Chemists (India), 73(5), 193-195; 2001. Chimica Acta Turcica (1984), 12(2), 305-14. Journal of Heterocyclic Chemistry, 21(6), 1689-98; 1984. Journal of Heterocyclic Chemistry (1980), 17(3), 607-8. Journal of Heterocyclic Chemistry (1969), 6(6), 835-40. Huaxue Shijie (2002), 43(7), 366-368. Indian Journal of Chemistry (1970), 8(6), 509-13. Ber. (1942), 75B 87-93. Journal of Medicinal Chemistry (1970), 13(5), 1015-17. Farmaco, EdizioneScientifica (1971), 26(1), 19-28. Journal of the Indian Chemical Society (1989), 66(2), 118-19. Journal of Heterocyclic Chemistry, 12(3), 581-3; 1975 European Journal of Medicinal Chemistry, 10(2), 121-4; 1975. Journal of Heterocyclic Chemistry (1977), 14(5), 853-5. Zhurnal Obshchei Khimii (1980), 50(4), 860-3. European Journal of Medicinal Chemistry (1996), 31(7-8), 597-606. Journal of Heterocyclic Chemistry (1980), 17(3), 607-8. Journal fuer Praktische Chemie (Leipzig), 332(1), 55-64; 1990). For example, compounds of formula 1 can be obtained by reacting a compound of formula VII-IX, with thiosemicarbazide in a suitable solvent such as water, C1-C4 alcohol in the presence of acid, preferably HCl, $H_3PO_4$, polyphosphoric acid, sulfuric acid, $MeSO_3OH$, etc. Compounds of formula 1 can also be obtained by reacting a compound of formula X with $FeCl_3$ as described in the reference cited above (Journal of Heterocyclic Chemistry, 12(3), 581-3; 1975; Pharm. Pharmacol. Commun. 2000, 6, 31-33; Russian J. Org. Chem. Vol 33, 1997, pp 567-568; Eur. J. Med. Chem. (1996) 31, 597-606;). Alternatively, compounds of formula 1 can be obtained by reacting a compound of formula VII, with thiosemicarbazide and phosphorous oxychloride at reflux, followed by hydrolysis (J. Heterocyclic Chem. 8: 835-837.).

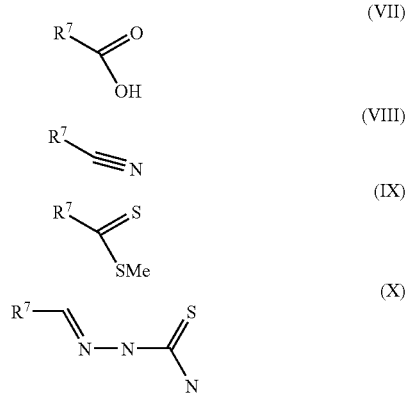

Numerous reagents that are well-known in the art may be used to couple 1 and 2a-c to form 3 by standard peptide coupling methods (2a) or the trimethylaluminum coupling method (2b) or a leaving group (halogen or a mixed anhydride) (2c) known in art of organic chemistry (Scheme I). Activation of the carboxylic acid 2a with oxalyl halide, thionyl chloride, carbodiimidazole, or chloro —($C_1$-$C_4$)alkyl-formate, in the prepsence of an appropriate base (e.g., tialkylamine, pyridine, dimethylaminopyridine or sodium carbonate, or the like) or carbodiimides with or without the use of known additives such as N-hydroxysuccinimide, 1-hydroxybenzotriazole, etc. can be used to facilitate coupling. Standard coupling agents include HATU (O-(7-azabenzotriazole-1-yl)-1,1,3,3,-tetramethyluronium hexafluorophosphate) or PyBOP (benzotriazole-1-yl)-oxy-tris-pyrrolidino-phosphonium hexafluorophosphate) or HBTU (O-benzotriazole-1-yl)-N,N,N',N'-tetramethyluronium hexafluorophosphate)/trialkylamine, or 1-hydroxybenzotriazole (HOBT)/1-(3-dimethylaminopropyl)-3-ethyl carbodiimide hydrochloride (EDAC)/trialkylamine (NEt3), in an appropriate solvent such as methylene chloride, chloroform, tetrahydrofuran (THF), acetonitrile, dimethylforamide (DMF), and the like or a mixture of two solvents to have reagents mixed well to form a clear solution. Peptide coupling agents or resins for solid phase synthesis such as Fmoc (Fluorenylmethylcarbonyl)-protected hydroxylamine bound to polystylene beads are common and well known in the literature. Deprotection of the Fmoc group under standard conditions using 20% piperidine in DMF. References: O-benzotriazol-1-yl-N,N,N',N'-tetramethyluronium hexafluorophosphate ("HBTU", Aldrich Chemical Company) and O-(7-azabenzotriazol-1-yl)-N,N,N',N'-tetramethyluronium hexafluorophosphate ("HATU", Aldrich) (See, Fieser, *Reagents for Organic Synthesis*, 1986, Wiley Interscience, New York, Vol. 12, p. 44; Hruby, *Biorganic Chemistry*: Peptides and Proteins, 1998, Oxford University press, New York, pp. 27-64; Muller, *Methoden Der Organischen Chemie*, Vierte Auflage—Synthese von Peptiden II—Houben Weyl, George-Thieme Verlag Stuttgart, 1974, Band XV/2). When optically active reagents are employed, reaction conditions, such as temperature, time and the selection of the base, must be carefully controlled to avoid racemization. The protected amino group or carboxylic acid group may be prepared by methods well known in the literature for amino acid protecting groups as described in Organic chemistry Journal, textbook such as "Protective Groups in Organic Syntehsis" by T. W. Green. Alternatively, the coupling can be performed by reacting 1 with an ester 2b in the presence of trialkylaluminum in an appropriate solvent, eg., THF, dioxane, toluene or a mixture of THF/toluene in an open or sealed tube at a temperature between 0° C.-120° C. until the complete conversion to the desired product (3 in Scheme I); preferred temperature is room temperature to 80° C.

Intermediate 3 of Scheme I, is deprotected to afford aminoamide 4 either through treatment with strong acid in the case of t-butoxycarbonyl or through hydrogenolysis in the case of carbobenzyloxycarbonyl. Specifically, t-BOC-3, on treatment with hydrochloric acid or trifluoroacetic acid in an organic solvent (e.g., dioxane, THF, or methylene chloride), at room temperature to 30° C. for about 1 hour to about 19 hours, affords the corresponding salts 4. Alternatively, CBZ-3 may be deprotected through catalytic hydrogenolysis in the presence of hydrogen (from about 1 to about 10 atmospheres), a heavy metal catalyst (e.g., palladium on carbon or palladium hydroxide on carbon, 1 to 10 percent catalyst loading, present at about 0.01 to about 0.50 times the of substrate), and a solvent (e.g., methanol, ethanol or ethyl acetate) at 20 to 50° C. for about 1 hour to about 19 hours.

The compound Formula I 10 in Scheme I may be prepared by the reaction of 4 with 9 where L is a leaving group (e.g., halide, mesylate, or triflate) and Z is as defined above. The reaction is carried out at 0 to 30° C. in an organic solvent (e.g., methylene chloride, ethyl acetate, or DMF) in the presence of an organic base (e.g., triethylamine, diisopropylethylamine, or N-methylmorpholine) for about 1 minute to about 24 hours.

Alternatively, the compound Formula I 10 may be prepared according to the procedure of Scheme II (Z-L is a carboxylic acid or L is a leaving group), employing the general conditions described for Scheme I. In Scheme II, R can be alkyl or benzyl. The coupling of 9 and 11 in Scheme II may be performed at a temperature of about 0 to 30° C. in an organic solvent (e.g., methylene chloride, dichloroethane, ethyl acetate, or DMF) in the presence of a base (e.g., triethylamine or diisopropylethylamine). When R is alkyl, either acidic or basic hydrolysis may be used to covert 12 to 13. If R is benzyl, catalytic hydrogenolysis may also be used to prepare 13.

dichloroethane, DMF, THF, MeOH, ethanol, about iso-propanol, t-butanol or toluene, at a temperature between room temperature to reflux, preferably at about room temperature to about 65° C.

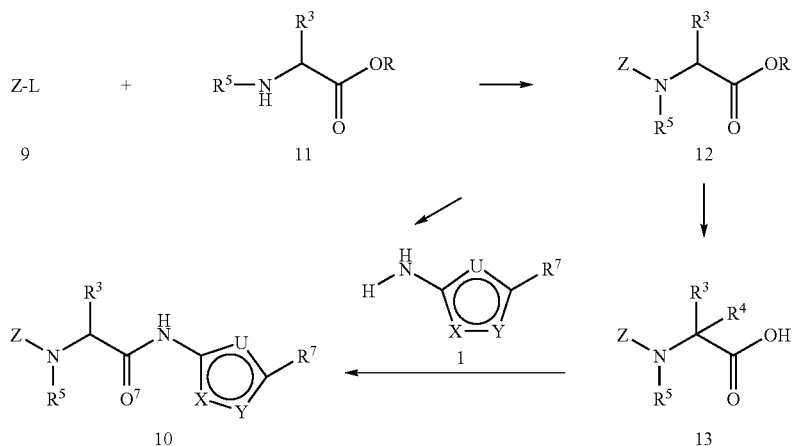

The above amide bond formation may be achieved by coupling the ester (12 in Scheme II) with 1 in the presence of trialkylaluminum (e.g., AlMe3) in an appropriate solvent, e.g., THF, toluene or a mixture of THF/toluene, or similar like solvents in an open or sealed tube at a temperature of about 0° C.-110° C. until there is complete conversion to the desired product (10 in Scheme II). Preferably, the temperature is about room temperature to about 80° C.

The ester group of $R^7$ may be converted to the corresponding amide using a coupling method similar to those described in Scheme I and II for amide bond formation (acid and amine with coupling agents to form an amide), or employing trimethylaluminum in an appropriate solvent or a mixture of solvents, such as THF/toluene to the corresponding amide (ester with an amine to form an amide). The olefin containing R7 group may be converted to a ketone, CHO, CH2OH, or COOH using ozonolysis followed by either reduction to give alcohol (by quenching with BH3.DMS, Journal of Organic Chemistry (1989), 54(6), 1430-2.), or ketone or aldehyde (by quenching with dimethylsulfide or triphenylphosphine).

The keto or formyl group of $R^7$ may be converted to the corresponding amine using a well-established reductive amination method by reacting a ketone with an appropriate amine with or without acid catalyst or Lewis acid catalyst $(Ti(iPrO)_4, ZnCl_2, NiCl_2,$ /sodium acetate/dry agents (such as activated molecular sieves 4A, anhydrous $Na_2SO_4$ or $MgSO_4$), and a reducing agent such as sodium triacetoxy borohydride, sodium cyanoborohydride, sodium borohydride, $Zn(BH_4)_2$, $Bu_3SnH$, $Bu_2SnClH$, $Bu_2SnIH$, decaborane, silical gel-$Zn(BH_4)_2$, $Et_3SiH$-trifluoroacetic acid, pyridine-BH3, phenylsilane-dibutyltin dichloride, or the corresponding polymer bound-$NaBH_4$, polymer bound-$NaBH_3CN$, polymer bound-$NaB(OAc)_3H$, or any reducing agent (e.g., hydrogenation, $Pd(OAc)_2$/potassium formate, $Pd/C/H_2$) that is known in the literature for reducing the imine bond to the corresponding amine in an appropriate solvent, such as dichloroethane, chloroform, 2-methoxyethyl ether, The starting materials used in the procedures of the above Schemes, the syntheses of which are not described above, are either commercially available, known in the art or readily obtainable from known compounds using methods that will be apparent to those skilled in the art.

The compounds of Formula I, and the intermediates shown in the above reaction schemes, may be isolated and purified by conventional procedures, such as recrystallization or chromatographic separation, such as on silica gel, either with an ethyl acetate/hexane elution gradient, a methylene chloride/methanol elution gradient, or a chloroform/methanol elution gradient. Alternatively, a reverse phase preparative HPLC or chiral HPLC separation technique may be used.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

Pharmaceutically acceptable salts of the compounds of Formula I may be prepared in a conventional manner by treating a solution or suspension of the corresponding free base or acid with one chemical equivalent of a pharmaceutically acceptable acid or base. Conventional concentration or crystallization techniques may be employed to isolate the salts. Suitable acids, include, but are not limited to, acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic and related acids. Suitable bases include, but are not limited to, sodium, potassium and calcium.

A compound of the Formula I of the present invention may be administered to mammals via either the oral, parenteral (such as subcutaneous, intravenous, intramuscular, intrasternal and infusion techniques), rectal, intranasal, topical or transdermal (e.g., through the use of a patch) routes. In general, these compounds are most desirably administered in doses ranging from about 0.1 mg to about 500 mg per day, in single or divided doses (i.e., from 1 to 4 doses per day), although variations will necessarily occur depending upon the species, weight, age and condition of the subject being treated, as well as the particular route of administration chosen. However, a dosage level that is in the range of about 0.1 mg/kg to about 5 gm/kg body weight per day, preferably from about 0.1 mg/kg to about 100 mg/kg body weight per day, is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dosage levels are first divided into several small doses for administration throughout the day.

A compound of the Formula I of the present invention may be administered alone or in combination with pharmaceutically acceptable carriers or diluents by either of the routes previously indicated, and such administration may be carried out in single or multiple doses. Suitable pharmaceutical carriers include solid diluents or fillers, sterile aqueous media and various non-toxic organic solvents, etc. The pharmaceutical compositions formed by combining a compound of the Formula I, or a pharmaceutically acceptable salt thereof, with a pharmaceutically acceptable inert carrier, can then be readily administered in a variety of dosage forms such as tablets, capsules, lozenges, troches, hard candies, powders, sprays, creams, salves, suppositories, jellies, gels, pastes, lotions, ointments, aqueous suspensions, injectable solutions, elixirs, syrups, and the like. Moreover, oral pharmaceutical compositions may be suitably sweetened and/or flavored.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing a compound of the Formula I of the present invention in either sesame or peanut oil or in aqueous propylene glycol may be employed. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The compounds of Formula I of the present invention are useful in inhibiting Aβ-peptide production (thus, gamma-secretase activity) in mammals, and therefore they are able to function as therapeutic agents in the treatment of the aforementioned disorders and diseases in an afflicted mammal.

The ability of compounds of the Formula I of this invention, and their pharmaceutically acceptable salts, to inhibit Aβ-peptide production (thus, gamma-secretase activity) may be determined using biological assays known to those of ordinary skill in the art, for example the assays described below.

The activity of compounds of the Formula I of the present invention in inhibiting gamma-secretase activity was determined in a solubilized membrane preparation generally according to the description provided in McLendon et al. Cell-free assays for β-secretase activity, *The FASEB Journal* (Vol. 14, December 2000, pp. 2383-2386). Using such assay, compounds of the present invention were determined to have an $IC_{50}$ activity for inhibiting gamma-secretase activity of less than about 100 micromolar.

The following Examples illustrate the present invention. It is to be understood, however, that the invention, as fully described herein and as recited in the claims, is not intended to be limited by the details of the following Examples.

Experimental Procedures

EXAMPLE 1

2-[2-(3,5-Difluoro-phenyl)-acetylamino]-pentanoic acid (5-tert-butyl-[1,3,4]-thiadiazol-2-yl)-amide A mixture of 3,5-di-fluoro-phenyl acetic acid (51.6 mg, 0.3 mmol), 2-amino-pentanoic acid (5-tert-butyl-[1,3,4]thiadiazol-2-yl)-amide (88 mg, 0.3 mmol), HBOT (43 mg, 0.315 mmol), EDC HCl (69 mg, 0.36 mmol.) and triethylamine (0.17 ml) in methylene chloride was stirred at room temperature until product formation or disappearance of starting material. The mixture was quenched with water and extracted with methylene chloride. The organic layer was separated, washed with dilute HCl, brine, dried over sodium sulfate and the solvent was removed at reduced pressure to provide the title compound as a cude oil. The oil was purified by Shimadzu HPLC to provide the title compound as a white solid (56 mg), LC-MS M+1=411.2, 1H NMR(CDCL3) 8.7 (d,1H, NH), 6.73(m,2H), 6.6(m,1H), 4.7(m,1H), 3.5(Abq, 2H), 1.6-1.9(m,2H), 1.3-1.6(m,2H), 1.5(s,9H), 0.92(t,3H) ppm.

EXAMPLE 2

2-[2-(3,5-Difluoro-phenyl)-acetylamino]-pentanoic acid [5-(2-phenyl-propylsulfanyl)-[1,3,4]thiadiazol-2-yl]-amide A mixture of 2-[2-(3,5-difluoro-phenyl)-acetylamino]-pentanoic acid (25.4 mg, 0.2 mmol), 5-(2-phenyl-propylsulfanyl)-[1,3,4]thiadiazol-2-ylamine (50 mg, 0.2 mmol), HBOT (29 mg, 0.21 mmol), EDC HCl (46 mg, 0.24 mmol.) and triethylamine (0.12 ml) in methylene chloride was stirred at room temperature until product formation or disappearance of starting material. The mixture was quenched with water and extracted with methylene chloride. The organic layer was separated, washed with dilute HCl, brine, dried over sodium sulfate and the solvent was removed at reduced pressure to provide the title compound as a cude oil. The oil was purified by Shimadzu HPLC to provide the title compound as a light yellow solid (26 mg), LC-MS M+1=505.0

EXAMPLE 3

2-(2-Hydroxy-3-methyl-butyrylamino)-pentanoic acid (5-tert-butyl-[1,3,4]thiadiazol-2-yl)-amide A mixture of 2-(S)hydroxyl-3-methyl-butyric acid (35.4 mg, 0.3 mmol), 2-amino-pentanoic acid (5-tert-butyl-[1,3,4] thiadiazol-2-yl)-amide (88 mg, 0.3 mmol), HBOT (43 mg, 0.21 mmol), EDC HCl (69 mg, 0.36 mmol.) and triethylamine (0.17 ml) in 2 ml of methylene chloride was stirred at room temperature until product formation or disappearance of starting material. The mixture was quenched with water and extracted with methylene chloride. The organic layer was separated, washed with dilute HCl, brine, dried over sodium sulfate and the solvent was removed at reduced pressure to provide the title compound as a cude oil. The oil was purified by Shimadzu HPLC to provide the title compound as a light yellow solid (44 mg), LC-MS M+1=357.1

The following compounds were prepared by the methods analogous to those described in Examples 1, 2, or 3.

2-[2-(3,5-Difluoro-phenyl)-acetylamino]-pentanoic acid (5-phenyl-[1,3,4]thiadiazol-2-yl)-amide, M+1=431.1

2-[2-(3,5-Difluoro-phenyl)-acetylamino]-pentanoic acid [5-(4-methoxy-phenyl)-[1,3,4]thiadiazol-2-yl]-amide, M+1=461.0, RT=2.7 min 2-[2-(3,5-Difluoro-phenyl)-acetylamino]-pentanoic acid [5-(3,4-dimethyl-benzylsulfanyl)-[1,3,4]thiadiazol-2-yl]-amide, M+1=504.9

2-[2-(3,5-Difluoro-phenyl)-acetylamino]-pentanoic acid (5-adamantan-1-yl-[1,3,4]thiadiazol-2-yl)-amid, M+1=489.1

2-[2-(3,5-Difluoro-phenyl)-acetylamino]-pentanoic acid [5-(4-chloro-benzyl)-[1,3,4]thiadiazol-2-yl]-amide, M+=478.9

2-[2-(3,5-Difluoro-phenyl)-acetylamino]-pentanoic acid [5-(3-trifluoromethyl-benzylsulfanyl)-[1,3,4]thiadiazol-2-yl]-amide, M+1=545.0

2-[2-(3,5-Difluoro-phenyl)-acetylamino]-pentanoic acid [5-(3-methoxy-benzylsulfanyl)-[1,3,4]thiadiazol-2-yl]-amide, M+1=507.0

2-[2-(3,5-Difluoro-phenyl)-acetylamino]-pentanoic acid [5-(2-fluoro-benzylsulfanyl)-[1,3,4]thiadiazol-2-yl]-amide, M+1=495.0

2-[2-(3,5-Difluoro-phenyl)-acetylamino]-pentanoic acid (5-propylsulfamoyl-[1,3,4]thiadiazol-2-yl)-amide, M+1=476.0

2-[2-(3,5-Difluoro-phenyl)-acetylamino]-pentanoic acid {5-[2-(3-trifluoromethyl-phenoxy)-ethylsulfanyl]-[1,3,4]thiadiazol-2-yl}-amide, M+1=574.9

2-[2-(3,5-Difluoro-phenyl)-acetylamino]-pentanoic acid [5-(3,4-dichloro-benzylsulfanyl)-[1,3,4]thiadiazol-2-yl]-amide, M+1=544.8

2-[2-(3,5-Difluoro-phenyl)-acetylamino]-pentanoic acid (5-dipropylsulfamoyl-[1,3,4]thiadiazol-2-yl)-amide, M+1=518.0

2-[2-(3,5-Difluoro-phenyl)-acetylamino]-pentanoic acid (5-benzylsulfanyl-[1,3,4]thiadiazol-2-yl)-amide, M+1=476.9

2-[2-(3,5-Difluoro-phenyl)-acetylamino]-pentanoic acid {5-[1-(2,4-dichloro-phenoxy)-ethyl]-[1,3,4]thiadiazol-2-yl}-amide, M+1=543.0

2-[2-(3,5-Difluoro-phenyl)-acetylamino]-pentanoic acid [5-(4-phenoxy-butylsulfanyl)-[1,3,4]thiadiazol-2-yl]-amide, M+1=535.0

2-[2-(3,5-Difluoro-phenyl)-acetylamino]-pentanoic acid {5-[2-(4-bromo-phenoxy)-ethylsulfanyl]-[1,3,4]thiadiazol-2-yl}-amide, M+1=586.8

2-[2-(3,5-Difluoro-phenyl)-acetylamino]-pentanoic acid (5-diethylsulfamoyl-[1,3,4]thiadiazol-2-yl)-amide, M+1=490.0

2-[2-(3,5-Difluoro-phenyl)-acetylamino]-pentanoic acid (5-ethylsulfamoyl-[1,3,4]thiadiazol-2-yl)-amide, M+1=461.9

2-[2-(3,5-Difluoro-phenyl)-acetylamino]-pentanoic acid (5-phenethylsulfanyl-[1,3,4]thiadiazol-2-yl)-amide, M+=491.0

2-(2-Hydroxy-2-phenyl-acetylamino)-pentanoic acid (5-tert-butyl-[1,3,4]thiadiazol-2-yl)-amide, M+1=391.2

2-(2-Hydroxy-3,3-dimethyl-butyrylamino)-pentanoic acid (5-tert-butyl-[1,3,4]thiadiazol-2-yl)-amide, M+1=371.2

2-(2-Hydroxy-3-methyl-butyrylamino)-pentanoic acid (5-tert-butyl-[1,3,4]thiadiazol-2-yl)-amide, M+1=357.2

2-[2-(3,5-Difluoro-phenyl)-2-(S)-2-hydroxy-acetylamino]-pentanoic acid (5-tert-butyl-[1,3,4]thiadiazol-2-yl)-amide, M+1=427.2

2-[2-(3,5-Difluoro-phenyl)-2-(R)-2-hydroxy-acetylamino]-pentanoic acid (5-tert-butyl-[1,3,4]thiadiazol-2-yl)-amide, M+1=427.2

2-[2-(5-Bromo-pyridin-3-yl)-acetylamino]-pentanoic acid (5-tert-butyl-[1,3,4]thiadiazol-2-yl)-amide, M+1=454.2

2-(2-Bicyclo[2.2.1]hept-2-yl-acetylamino)-pentanoic acid (5-tert-butyl-[1,3,4]thiadiazol-2-yl)-amide, M+1=393.3

2-[2-(3,5-Difluoro-phenyl)-acetylamino]-pentanoic acid (5-ethyl-[1,3,4]thiadiazol-2-yl)-amide, M+1=383.2

2-(2-Hydroxy-3-methyl-butyrylamino)-pentanoic acid (5-ethyl-[1,3,4]thiadiazol-2-yl)-amide, M+1=329.2

2-[2-(5-Bromo-pyridin-3-yl)-acetylamino]-pentanoic acid (5-ethyl-[1,3,4]thiadiazol-2-yl)-amide, M+1=428.2

2-(2-Bicyclo[2.2.1]hept-2-yl-acetylamino)-pentanoic acid (5-ethyl-[1,3,4]thiadiazol-2-yl)-amide, M+1=365.3

2-[2-(3,5-Difluoro-phenyl)-acetylamino]-pentanoic acid (5-methyl-[1,3,4]thiadiazol-2-yl)-amide, M+1=369.1

2-(S)-(2-(S)-Hydroxy-2-phenyl-acetylamino)-pentanoic acid (5-methyl-[1,3,4]thiadiazol-2-yl)-amide, M+1=349.1

2-(S)-(2-(R)-Hydroxy-2-phenyl-acetylamino)-pentanoic acid (5-methyl-[1,3,4]thiadiazol-2-yl)-amide, M+1=349.1

Hydroxy-phenyl-acetic acid [1-(5-methyl-[1,3,4]thiadiazol-2-ylcarbamoyl)-butylcarbamoyl]-phenyl-methyl ester, M+1=483.2

2-(2-Hydroxy-3,3-dimethyl-butyrylamino)-pentanoic acid (5-methyl-[1,3,4]thiadiazol-2-yl)-amide, M+1=329.2

2-(2-Hydroxy-3-methyl-butyrylamino)-pentanoic acid (5-methyl-[1,3,4]thiadiazol-2-yl)-amide, M+1=315.1

2-(S)-[2-(R)-(3,5-Difluoro-phenyl)-2-hydroxy-acetylamino]-pentanoic acid (5-methyl-[1,3,4]thiadiazol-2-yl)-amide, M+1=385.2

2-(S)-[2-(S)-(3,5-Difluoro-phenyl)-2-hydroxy-acetylamino]-pentanoic acid (5-methyl-[1,3,4]thiadiazol-2-yl)-amide, M+1=385.2

2-[2-(3,5-Difluoro-phenyl)-acetylamino]-N-(5-ethylsulfanyl-[1,3,4]thiadiazol-2-yl)-butyramide, RT=2.3 min, M+1=401.3

2-[2-(3,5-Difluoro-phenyl)-acetylamino]-N-[5-(2-dimethylamino-ethylsulfanyl)-[1,3,4]thiadiazol-2-yl]-butyramide, RT=1.4 min, M+1=44.5

2-[2-(3,5-Difluoro-phenyl)-acetylamino]-N-(5-ethoxyethyl-[1,3,4]thiadiazol-2-yl)-butyramide, RT=2.1 min, M+1=399.3

2-[2-(3,5-Difluoro-phenyl)-acetylamino]-N-(5-dimethylamino-[1,3,4]thiadiazol-2-yl)-butyramide, RT=2.0 min, M+1=384.5

2-[2-(3,5-Difluoro-phenyl)-acetylamino]-N-(5-isobutyl-[1,3,4]thiadiazol-2-yl)-butyramide, RT=2.3 min, M+1=397.4

2-[2-(3,5-Difluoro-phenyl)-acetylamino]-N-(5-phenyl-[1,3,4]thiadiazol-2-yl)-butyramide, RT=2.5 min, M+1=417.3

2-[2-(3,5-Difluoro-phenyl)-acetylamino]-N-(5-isopropyl-[1,3,4]thiadiazol-2-yl)-butyramide, RT=2.2 min, M+1=383.5

N-(5-Benzyl-[1,3,4]thiadiazol-2-yl)-2-[2-(3,5-difluoro-phenyl)-acetylamino]-butyramide, RT=2.5 min, M+1=431.5

2-[2-(3,5-Difluoro-phenyl)-acetylamino]-N-(5-phenoxymethyl-[1,3,4]thiadiazol-2-yl)-butyramide, RT=2.6 min, M+1=447.5

N-[5-(3-Chloro-phenyl)-[1,3,4]thiadiazol-2-yl]-2-[2-(3,5-difluoro-phenyl)-acetylamino]-butyramide, RT=2.7 min, M+1=451.3

N-(5-Cyclobutyl-[1,3,4]thiadiazol-2-yl)-2-[2-(3,5-difluoro-phenyl)-acetylamino]-butyramide, RT=2.4 min, M+1=395.5

2-[2-(3,5-Difluoro-phenyl)-acetylamino]-N-[5-(5-methyl-3-phenyl-isoxazol-4-yl)-[1,3,4]thiadiazol-2-yl]-butyramide, RT=2.7 min, M+1=498.5

2-[2-(3,5-Difluoro-phenyl)-acetylamino]-N-(5-methoxymethyl-[1,3,4]thiadiazol-2-yl)-butyramide, RT=2.0 min, M+1=385.5

2-[2-(3,5-Difluoro-phenyl)-acetylamino]-N-(5-isopropyl-sulfanyl-[1,3,4]thiadiazol-2-yl)-butyramide, RT=2.6 min, M+1=415.5

2-[2-(3-Phenoxy-phenyl)-acetylamino]-pentanoic acid (5-cyclohexyl-[1,3,4]thiadiazol-2-yl)-amide, M+1=493.5

2-[2-(3-Phenoxy-phenyl)-acetylamino]-pentanoic acid (5-methylsulfamoyl-[1,3,4]thiadiazol-2-yl)-amide, M+1=504.6, RT=2.7 min 2-(5-{2-[2-(3-Phenoxy-phenyl)-acetylamino]-pentanoylamino}-[1,3,4]thiadiazol-2-ylsulfanyl)-propionic acid ethyl ester, M+1=543.6, RT=3.0 min 2-[2-(3-Phenoxy-phenyl)-acetylamino]-pentanoic acid (5-phenethyl-[1,3,4]thiadiazol-2-yl)-amide, M+1=515.4, RT=3.0 min 2-[2-(3-Phenoxy-phenyl)-acetylamino]-pentanoic acid [5-(1-phenoxy-ethyl)-[1,3,4]thiadiazol-2-yl]-amide, M+1=531.4, RT=3.0 min 2-[2-(3,5-Difluoro-phenyl)-2-hydroxy-acetylamino]-pentanoic acid (5-methyl-[1,3,4]thiadiazol-2-yl)-amide, RT=2.0 min, M+1=385.2

2-[2-(3,5-Difluoro-phenyl)-acetylamino]-pentanoic acid (5-cyclopropyl-[1,3,4]thiadiazol-2-yl)-amide, RT=2.3 min, M+1=395.3

2-[2-(3,5-Difluoro-phenyl)-acetylamino]-pentanoic acid (5-formyl-[1,3,4]thiadiazol-2-yl)-amide, RT=2.1 min, M+1=383.2

2-[2-(2,5-Difluoro-phenyl)-acetylamino]-pentanoic acid (5-tert-butyl-[1,3,4]thiadiazol-2-yl)-amide, RT=2.4 min, M+1=411.3

2-[2-(3,5-Difluoro-phenyl)-acetylamino]-pentanoic ethyl-propyl)-[1,3,4]thiadiazol-2-yl]-amide, RT=2.6 min, M+1=425.3

2-[2-(3,5-Difluoro-phenyl)-acetylamino]-pentanoic acid [5-(2,4,4-trimethyl-pentyl)-[1,3,4]thiadiazol-2-yl]-amide, RT=3.0 min, M+1=467.4

2-[2-(3,5-Difluoro-phenyl)-acetylamino]-pentanoic acid [5-(1-ethyl-pentyl)-[1,3,4]thiadiazol-2-yl]-amide, RT=2.8 min, M+1=453.5

2-(2-(S)-Hydroxy-3,3-dimethyl-butyrylamino)-pentanoic acid [5-(1-ethyl-pentyl)-[1,3,4]thiadiazol-2-yl]-amide, RT=2.7 min, M+1=413.5

2-(2-(R)-Hydroxy-3,3-dimethyl-butyrylamino)-pentanoic acid [5-(1-ethyl-pentyl)-[1,3,4]thiadiazol-2-yl]-amide, RT=2.7 min, M+1=413.5

2-(2-(R)-Hydroxy-3,3-dimethyl-butyrylamino)-pentanoic acid [5-(1-ethyl-propyl)-[1,3,4]thiadiazol-2-yl]-amide, RT=2.3 min, M+1=385.5

2-(2-(S)-Hydroxy-3,3-dimethyl-butyrylamino)-pentanoic acid [5-(1-ethyl-propyl)-[1,3,4]thiadiazol-2-yl]-amide, RT=2.3 min, M+1=385.5

2-(2-(R)-Hydroxy-2-phenyl-acetylamino)-pentanoic acid [5-(1-ethyl-propyl)-[1,3,4]thiadiazol-2-yl]-amide, RT=2.2 min, M+1=405.5

2-(2-(S)-Hydroxy-2-phenyl-acetylamino)-pentanoic acid [5-(1-ethyl-propyl)-[1,3,4]thiadiazol-2-yl]-amide, RT=2.2 min, M+1=405.5

2-[2-(3,5-Difluoro-phenyl)-acetylamino]-pentanoic acid [5-(1,1-dimethyl-but-3-enyl)-[1,3,4]thiadiazol-2-yl]-amide, RT=2.7 min, M+1=437.1

2-(2-(R)-Hydroxy-2-phenyl-acetylamino)-pentanoic acid [5-(1 ethyl-pentyl)-[1,3,4]thiadiazol-2-yl]-amide, RT=2.6 min, M+1=433.5

2-(2-(S)-Hydroxy-2-phenyl-acetylamino)-pentanoic acid [5-(1-ethyl-pentyl)-[1,3,4]thiadiazol-2-yl]-amide, RT=2.6 min, M+1=433.5

2-[2-(3,5-Difluoro-phenyl)-acetylamino]-pentanoic acid [5-(1,1-dimethyl-butyl)-[1,3,4]thiadiazol-2-yl]-amide, RT=2.7 min, M+1=439.5

2-(2-Hydroxy-2-phenyl-acetylamino)-pentanoic acid [5-(1,1-dimethyl-butyl)-[1,3,4]thiadiazol-2-yl]-amide, white solid, RT=2.0 min, M+1=419.5

2-(2-Hydroxy-3,3-dimethyl-butyrylamino)-pentanoic acid [5-(1,1-dimethyl-butyl)-[1,3,4]thiadiazol-2-yl]-amide, white solid, RT=2.6 min, M+1=399.5

2-(2-Hydroxy-3-methyl-butyrylamino)-pentanoic acid [5-(1,1-dimethyl-butyl)-[1,3,4]thiadiazol-2-yl]-amide, white solid, RT=2.4 min, M+1=385.5

2-[2-(3,5-Difluoro-phenyl)-2-(R)-hydroxy-acetylamino]-pentanoic acid [5-(1,1-dimethyl-butyl)-[1,3,4]thiadiazol-2-yl]-amide, white solid, RT=2.7 min, M+1=455.5

2-[2-(3,5-Difluoro-phenyl)-2-(S)-hydroxy-acetylamino]-pentanoic acid [5-(1,1-dimethyl-butyl)-[1,3,4]thiadiazol-2-yl]-amide, white solid, RT=2.7 min, M+1=455.5

2-[2-(5-Bromo-pyridin-3-yl)-acetylamino]-pentanoic acid [5-(1,1-dimethyl-butyl)-[1,3,4]thiadiazol-2-yl]-amide, RT=2.5 min, M+1=484.4

2-[2-(3-Trifluoromethoxy-phenyl)-acetylamino]-pentanoic acid [5-(1,1-dimethyl-butyl)-[1,3,4]thiadiazol-2-yl]-amide, RT=3.0 min, M+1=487.5

2-[2-(3,5-Difluoro-phenyl)-acetylamino]-pentanoic acid [5-(1-methyl-but-3-enyl)-[1,3,4]thiadiazol-2-yl]-amide, LC-MS RT=2.6 min, M+1=423.2

2-[2-(3,5-Difluoro-phenyl)-acetylamino]-N-[5-(1-methyl-but-3-enyl)-[1,3,4]thiadiazol-2-yl]-butyramide, LC-MS RT=2.4 min, M+1=409.2

2-[2-(3,5-Difluoro-phenyl)-acetylamino]-pentanoic acid [5-(1-methyl-butyl)-[1,3,4]thiadiazol-2-yl]-amide, LC-MS RT=2.5 min, M+1=425.5

2-[2-(3,5-Difluoro-phenyl)-acetylamino]-N-[5-(1-methyl-butyl)-[1,3,4]thiadiazol-2-yl]-butyramide, LC-MS RT=2.5 min, M+1=411.4

2-[2-(3,5-Difluoro-phenyl)-acetylamino]-N-[5-(1,1-dimethyl-but-3-enyl)-[1,3,4]thiadiazol-2-yl]-butyramide, LC-MS RT=2.6 min, M+1=423.4

2-[2-(3,5-Difluoro-phenyl)-acetylamino]-pentanoic acid [5-(3,3-dimethoxy-1,1-dimethyl-propyl)-[1,3,4]thiadiazol-2-yl]-amide, LC-MS RT=2.6 min, M+1=485.0

2-(2-Hydroxy-3,3-dimethyl-butyrylamino)-pentanoic acid [5-(1,1-dimethyl-but-3-enyl)-[1,3,4]thiadiazol-2-yl]-amide, 1H NMR (CDCl3) δ 7.7 (d,1H), 5.65(m,1H), 5.1(m, 2H), 4.7(m,1H), 3.8(s,1H), 2.5(d,2H), 1.7-2.0(m,2H), 1.5-1.6 (m,2H), 1.45(s,6H), 0.98(s,9H), 0.94(t,3H)ppm 2-(2-Hydroxy-2-phenyl-acetylamino)-pentanoic acid [5-(1,1-dimethyl-but-3-enyl)-[1,3,4]thiadiazol-2-yl]-amide, LC-MS RT=2.6 min, M+1=416.9

2-(2-Hydroxy-3-methyl-butyrylamino)-pentanoic acid [5-(1,1-dimethyl-but-3-enyl)-[1,3,4]thiadiazol-2-yl]-amide, LC-MS RT=2.4 min, M+1=383.0

2-[2-(3,5-Difluoro-phenyl)-2-(S)-2-hydroxy-acetylamino]-pentanoic acid [5-(1,1-dimethyl-but-3-enyl)-[1,3,4] thiadiazol-2-yl]-amide, LC-MS RT=2.9 min, M+1=452.9

2-[2-(3,5-Difluoro-phenyl)-2-(R)-2-hydroxy-acetylamino]-pentanoic acid [5-(1,1-dimethyl-but-3-enyl)-[1,3,4] thiadiazol-2-yl]-amide, LC-MS RT=2.8 min, M+1=452.9

2-(2-Hydroxy-3,3-dimethyl-butyrylamino)-pentanoic acid (5-cyclopropyl-[1,3,4]thiadiazol-2-yl)-amide, LC-MS RT=2.2 min, M+1=355.0

2-(2-Hydroxy-3-methyl-butyrylamino)-pentanoic acid (5-cyclopropyl-[1,3,4]thiadiazol-2-yl)-amide, LC-MS RT=2.0 min, M+1=341.0

2-[2-(3,5-Difluoro-phenyl)-2-hydroxy-acetylamino]-pentanoic acid (5-cyclopropyl-[1,3,4]thiadiazol-2-yl)-amide, LC-MS RT=2.3 min, M+1=410.9

2-(2-Hydroxy-2-phenyl-acetylamino)-pentanoic acid (5-cyclopropyl-[1,3,4]thiadiazol-2-yl)-amide, LC-MS RT=2.2 min, M+1=374.9

2-[2-(3,5-Difluoro-phenyl)-acetylamino]-pentanoic acid (5-(2-chloro-1,1-dimethyl-ethyl)-[1,3,4]thiadiazol-2-yl)-amide, LC-MS RT=2.6 min, M+1=444.8

2-[2-(3,5-Difluoro-phenyl)-acetylamino]-pentanoic acid [5-(2-hydroxy-1,1-dimethyl-ethyl)-[1,3,4]thiadiazol-2-yl]-amide, LC-MS RT=2.1 min, M+1=426.9

2-(5-{2-[2-(3,5-Difluoro-phenyl)-acetylamino]-pentanoylamino}-[1,3,4]thiadiazol-2-ylsulfanyl)-2-methyl-propionic acid ethyl ester, LC-MS RT=2.8 min, M+1=500.8

2-[2-(3,5-Difluoro-phenyl)-acetylamino]-pentanoic acid {5-[(isopropyl-phenyl-carbamoyl)-methylsulfanyl]-[1,3,4] thiadiazol-2-yl}-amide, LC-MS RT=2.8 min, M+1=561.8

2-[2-(3,5-Difluoro-phenyl)-acetylamino]-pentanoic acid [5-(3-fluoro-benzylsulfanyl)-[1,3,4]thiadiazol-2-yl]-amide, LC-MS RT=2.9 min, M+1=494.8

2-[2-(3,5-Difluoro-phenyl)-acetylamino]-pentanoic acid [5-(4-trifluoromethyl-pyrimidin-2-ylsulfanyl)-[1,3,4]-thiadiazol-2-yl]-amide, 1H NMR(CDCl3/CD3OD)δ 8.74(d,1H), 7.37(d,1H), 6.70(m,2H0, 6.57(m,1H), 4.51(m,1H), 3.43(s, 2H), 1.71(m, 1H), 1.69(m,1H), 1.26(m,2H), 0.87(t,3H) ppm.

2-[2-(3,5-Difluoro-phenyl)-acetylamino]-pentanoic acid [5-(1-methyl-allyl)-[1,3,4]thiadiazol-2-yl]-amide, LC-MS RT=2.6 min, M+1=409.0

2-[2-(3,5-Difluoro-phenyl)-acetylamino]-pentanoic acid [5-(1-methyl-propenyl)-[1,3,4]thiadiazol-2-yl]-amide, LC-MS RT=2.6 min, M+1=409.0

2-[2-(3,5-Difluoro-phenyl)-acetylamino]-pentanoic acid [5-(2-benzyloxy-1,1-dimethyl-ethyl)-[1,3,4]thiadiazol-2-yl]-amide, LC-MS RT=3.0 min, M+1=517.0

2-[2-(3,5-Difluoro-phenyl)-acetylamino]-N-[3-(toluene-4-sulfonylamino)-[1,2,4]thiadiazol-5-yl]-butyramide, LC-MS RT=2.5 min, M+1=510.3

2-[2-(3,5-Difluoro-phenyl)-acetylamino]-pentanoic acid (3-ethylsulfanyl-[1,2,4]thiadiazol-5-yl)-amide, LC-MS RT=2.7 min, M+1=415.2

2-[2-(3,5-Difluoro-phenyl)-acetylamino]-pentanoic acid (3-methanesulfonyl-[1,2,4]thiadiazol-5-yl)-amide, LC-MS RT=2.3 min, M+1=433.2

2-[2-(3,5-Difluoro-phenyl)-acetylamino]-pentanoic acid [3-(4-nitro-benzenesulfonylamino)-[1,2,4]thiadiazol-5-yl]-amide, LC-MS RT=2.6 min, M+1=555.3

2-[2-(3,5-Difluoro-phenyl)-acetylamino]-pentanoic acid (3-p-tolylamino-[1,2,4]thiadiazol-5-yl)-amide, LC-MS RT=2.4 min, M+1=460.4

2-[2-(3,5-Difluoro-phenyl)-acetylamino]-pentanoic acid (3-methyl-[1,2,4]thiadiazol-5-yl)-amide, LC-MS RT=2.1 min, M+1=369.2

EXAMPLE 4

2-[2-(3,5-Difluoro-phenyl)-acetylamino]-pentanoic acid [5-(1,1-dimethyl-2-oxiranyl-ethyl)-[1,3,4]thiadiazol-2-yl]-amide A mixture of 2-[2-(3,5-difluoro-phenyl)-acetylamino]-pentanoic acid [5-(1,1-dimethyl-but-3-enyl)-[1,3,4]thiadiazol-2-yl]-amide (196 mg, 0.45 mmol) and ~60% pure m-chloroperbenzoic acid (109 mg, 0.45 mmol) in methylene chloride was stirred for 4 hr. The mixture was quenched with water, saturated Na$_2$S$_2$O$_3$ and extracted with methylene chloride. The organic layer was washed with brine, separated, dried, and concentrated to give 114 mg of crude material with a mixture of desired title compound and undesired N-oxide and recovered starting material. The crude material was purified by HPLC and the title compound was isolated, LC-MS, RT=2.3 min, M=1=453.5

EXAMPLE 5

2-[2-(3,5-Difluoro-phenyl)-acetylamino]-pentanoic acid [5-(1,1-dimethyl-3-oxo-propyl)-[1,3,4]thiadiazol-2-yl]-amide A stream of ozone was generated and passed through a solution of 2-[2-(3,5-difluoro-phenyl)-acetylamino]-pentanoic acid [5-(1,1-dimethyl-but-3-enyl)-[1,3,4]thiadiazol-2-yl]-amide (631 mg, 1.445 mmol) in 40 ml of methylene chloride until the mixture turned to blue solution or until the disappearance of starting material at −78° C. The mixture was stirred at −78° C. for 10 min, then the excess ozone was replaced with N$_2$ at −78° C. The mixture was quenched with excess of dimethylsulfide and stirred at r.t. overnight. The mixture was concentrated to dryness, purified by Shimadzu HPLC to give the title compound as a yellow solid, RT=2.3 min, M+1=439.5.

3-(5-{2-[2-(3,5-Difluoro-phenyl)-acetylamino]-pentanoylamino}-[1,3,4]thiadiazol-2-yl)-3-methyl-butyric acid, was prepared as described above in which the ozonolysis provided small quantity of the title compound that was isolated as the title carboxylic acid, RT=2.1 min, M+1=455.5

The following examples were prepared by the method analogous to that described in Example 5 starting with an appropriate olefin and ozone, followed by quenching with dimethylsulfide.

2-[2-(3,5-Difluoro-phenyl)-acetylamino]-pentanoic acid [5-(1-methyl-3-oxo-propyl)-[1,3,4]thiadiazol-2-yl]-amide, LC-MS RT=2.1 min, M+1=425.5

2-[2-(3,5-Difluoro-phenyl)-acetylamino]-N-[5-(1-methyl-3-oxo-propyl)-[1,3,4]thiadiazol-2-yl]-butyramide, APCI, M+1=411.1

2-[2-(3,5-Difluoro-phenyl)-acetylamino]-N-[5-(1,1-dimethyl-3-oxo-propyl)-[1,3,4]thiadiazol-2-yl]-butyramide, LC-MS RT=2.2 min, M+1=424.9

2-[2-(3,5-Difluoro-phenyl)-2-hydroxy-acetylamino]-pentanoic acid [5-(1,1-dimethyl-3-oxo-propyl)-[1,3,4]thiadiazol-2-yl]-amide, LC-MS RT=2.4 min, M+1=454.9

2-[2-(3,5-Difluoro-phenyl)-acetylamino]-pentanoic acid (5-acetyl-[1,3,4]thiadiazol-2-yl)-amide, LC-MS RT=2.3 min, M+1=396.9

EXAMPLE 7

2-[2-(3,5-Difluoro-phenyl)-acetylamino]-pentanoic acid [5-(1,1-dimethyl-2-oxo-ethyl)-[1,3,4]thiadiazol-2-yl]-amide A mixture of 2-[2-(3,5-difluoro-phenyl)-acetylamino]-pentanoic acid [5-(2-hydroxy-1,1-dimethyl-ethyl)-[1,3,4]thiadiazol-2-yl]-amide (40 mg, 0.93 mmol) and Dess-Martin periodinane (1,1,1-tris(acetyloxy)-1,1-dihydro-1,2-benziodoxol-3-(1H)-one) (90 mg) in methylene chloride (3 ml) was stirred at rt for 3 hr. The mixture was quenched with water, methylene chloride and filtered through celite. The filtrate was transferred to separatory funnel and the organic layer was separated, dried and concentrated to give 42 mg of crude material. The crude material was purified by silica gel column chromatography using methylene chloride to 1% methanol in methylene chloride as eluent to give 20 mg of the title compound as a tan glass solid. APCI M+1=425.2.

EXAMPLE 8

2-[2-(3,5-Difluoro-phenyl)-acetylamino]-pentanoic acid [5-(3-isopropylamino-1,1-dimethyl-propyl)-[1,3,4]thiadiazol-2-yl]-amide A mixture of 2-[2-(3,5-difluoro-phenyl)-acetylamino]-pentanoic acid [5-(1,1-dimethyl-3-oxo-propyl)-[1,3,4]thiadiazol-2-yl]-amide (88 mg, 0.2 mmol), isopropylamine (0.09 ml) in dichloroethane (1 ml) and methylene chloride (1 ml) was stirred at r.t. for 10 min, sodium triacetoxyborohydride (76 mg) was added and the resulting mixture was stirred at r.t. overnight. The mixture was quenched with water, diluted with sodium hydroxide, and extracted with methylene chloride. The organic layer was separated, dried over $Na_2SO_4$, filtered and concentrated to dryness. The residue was purified by silica gel column chromatography using 3-5% methanol in methylene chloride, then 5% methanol/0.5% ammonium hydroxide in methylene chloride as eluent to give the title compound as a free base form. The free base was treated with 4 N HCl in doxane (0.1 ml) in methylene chloride (1 ml) and concentrated to dryness. The residue was triturated with hexane, pumped to dryness to give a white solid, LC-MS RT=1.8 min, M+1=481.9.

EXAMPLE 9

2-[2-(3,5-Difluoro-phenyl)-acetylamino]-pentanoic acid [5-(3-isopropylamino-1-methyl-propyl)-[1,3,4]thiadiazol-2-yl]-amide A mixture of 2-[2-(3,5-difluoro-phenyl)-acetylamino]-pentanoic acid [5-(1-methyl-3-oxo-propyl)-[1,3,4]thiadiazol-2-yl]-amide (63 mg, 0.148 mmol), isopropylamine (0.2 ml) in dichloroethane (1 ml) and methylene chloride (1 ml) was stirred at r.t. for 10 min. Sodium cyanoborohydride (70 mg), acetic acid (0.1 ml), and sodium sulphate were added and the resulting mixture was stirred at 45-50° C. overnight. The mixture was quenched with water, basified with saturated sodium carbonate, extracted with methylene chloride. The organic layer was separated, dried over Na2SO4, filtered and concentrated to dryness. The residue was purified by Shimadzu HPLC to give the title compound LC-MS RT=1.7 min, M+1=467.9.

The following Examples were prepared by the method analogous to that described in Examples 8 or 9 starting from an appropriate aldehyde or ketone and an appropriate amine in an appropriate solvent or a mixture of solvents selected from methylene chloride, dichloroethane, THF, or DMF in the presence of a reducing agent selected from $NaBH_3CN$ or $NaB(OAc)_3H$ with or without acetic acid.

2-[2-(3,5-Difluoro-phenyl)-acetylamino]-pentanoic acid {5-[1,1-dimethyl-3-(2,2,2-trifluoro-ethylamino)-propyl]-[1,3,4]thiadiazol-2-yl}-amide, LC-MS, RT=1.6 min, M+1=522.6

2-[2-(3,5-Difluoro-phenyl)-acetylamino]-N-[5-(3-ethylamino-1-methyl-propyl)-[1,3,4]thiadiazol-2-yl]-butyramide HCl salt, LC-MS, RT=1.8 min, M+1=440.0

2-[2-(3,5-Difluoro-phenyl)-acetylamino]-N-[5-(3-isopropylamino-1-methyl-propyl)-[1,3,4]thiadiazol-2-yl]-butyramide, HCl salt, LC-MS, RT=1.6 min, M+1=453.9

2-[2-(3,5-Difluoro-phenyl)-acetylamino]-N-[5-(3-isopropylamino-1,1-dimethyl-propyl)-[1,3,4]thiadiazol-2-yl]-butyramide, LC-MS, RT=1.7 min, M+1=467.9

2-[2-(3,5-Difluoro-phenyl)-acetylamino]-pentanoic acid [5-(3-ethylamino-1,1-dimethyl-propyl)-[1,3,4]thiadiazol-2-yl]-amide, LC-MS, RT=1.9 min, M+1=467.9

2-[2-(3,5-Difluoro-phenyl)-acetylamino]-pentanoic acid [5-(3-dimethylamino-1,1-dimethyl-propyl)-[1,3,4]thiadiazol-2-yl]-amide HCl salt, LC-MS, RT=1.6 min, M+1=468.9

2-[2-(3,5-Difluoro-phenyl)-acetylamino]-pentanoic acid [5-(1,1-dimethyl-3-propylamino-propyl)-[1,3,4]thiadiazol-2-yl]-amide, HCl salt, LC-MS, RT=1.9 min, M+1=483.0

2-[2-(3,5-Difluoro-phenyl)-acetylamino]-pentanoic acid {5-[3-(2-hydroxy-ethylamino)-1,1-dimethyl-propyl]-[1,3,4]thiadiazol-2-yl}-amide, HCl salt, LC-MS, RT=1.8 min, M+1=484.9

2-[2-(3,5-Difluoro-phenyl)-acetylamino]-pentanoic acid [5-(3-tert-butylamino-1,1-dimethyl-propyl)-[1,3,4]thiadiazol-2-yl]-amide formic acid salt, LC-MS, RT=1.7 min, M+1=496.0

2-[2-(3,5-Difluoro-phenyl)-acetylamino]-pentanoic acid [5-(3-cyclopropylamino-1,1-dimethyl-propyl)-[1,3,4]thiadiazol-2-yl]-amide formic acid salt, LC-MS, RT=1.9 min, M+1=480.2

2-[2-(3,5-Difluoro-phenyl)-acetylamino]-pentanoic acid [5-(1,1-dimethyl-3-pyrrolidin-1-yl-propyl)-[1,3,4]thiadiazol-2-yl]-amide formic acid salt, LC-MS, RT=1.7 min, M+1=494.0

2-[2-(3,5-Difluoro-phenyl)-acetylamino]-pentanoic acid [5-(1,1-dimethyl-3-morpholin-4-yl-propyl)-[1,3,4]thiadiazol-2-yl]-amide formic acid salt, LC-MS, RT=1.5 min, M+1=510.0

2-[2-(3,5-Difluoro-phenyl)-acetylamino]-pentanoic acid {5-[3-(1-ethyl-propylamino)-1,1-dimethyl-propyl]-[1,3,4]thiadiazol-2-yl}-amide formic acid salt, LC-MS, RT=1.8 min, M+1=510.0

2-[2-(3,5-Difluoro-phenyl)-2-hydroxy-acetylamino]-pentanoic acid [5-(3-cyclopropylamino-1,1-dimethyl-propyl)-[1,3,4]thiadiazol-2-yl]-amide formic acid salt, LC-MS, RT=1.8 min, M+1=495.9

2-[2-(3,5-Difluoro-phenyl)-acetylamino]-pentanoic acid (5-{3-[formyl-(2,2,2-trifluoro-ethyl)-amino]-1,1-dimethyl-propyl}-[1,3,4]thiadiazol-2-yl)-amide, LC-MS, RT=2.6 min, M+1=549.9

2-[2-(3,5-Difluoro-phenyl)-2-hydroxy-acetylamino]-pentanoic acid (5-{3-[formyl-2,2,2-trifluoro-ethyl)-amino]-1,1-dimethyl-propyl}-[1,3,4]thiadiazol-2-yl)amide, LC-MS, RT=2.5 min, M+1=566.9

2-[2-(3,5-Difluoro-phenyl)-acetylamino]-pentanoic acid {5-[1-(3-methyl-butylamino)-ethyl]-[1,3,4]thiadiazol-2-yl}-amide, HCl salt, LC-MS, RT=1.9 min, M+1=468.0

2-[2-(3,5-Difluoro-phenyl)-acetylamino]-pentanoic acid [5-(1-butylamino-ethyl)-[1,3,4]thiadiazol-2-yl]-amide, HCl salt, LC-MS, RT=1.9 min, M+1=454.9

2-[2-(3,5-Difluoro-phenyl)-acetylamino]-pentanoic acid {5-[1-(3,3-dimethyl-butylamino)-ethyl]-[1,3,4]thiadiazol-2-yl}-amide HCl salt, LC-MS, RT=2.2 min, M+1=482.0

2-[2-(3,5-Difluoro-phenyl)-acetylamino]-pentanoic acid [5-(1-cyclopropylamino-ethyl)-[1,3,4]thiadiazol-2-yl]-amide HCl salt, LC-MS, RT=1.7 min, M+1=437.9

2-[2-(3,5-Difluoro-phenyl)-acetylamino]-pentanoic acid {5-[1-(4-methyl-piperazin-1-yl-)-ethyl]-[1,3,4]thiadiazol-2-yl}-amide formic acid salt, LC-MS, RT=1.7 min, M+1=481.0

2-[2-(3,5-Difluoro-phenyl)-acetylamino]-pentanoic acid {5-[1-(4-chloro-benzylamino)-ethyl]-[1,3,4]thiadiazol-2-yl}-amide formic acid salt, LC-MS, RT=2.3 min, M+1=521.9

2-[2-(3,5-Difluoro-phenyl)-acetylamino]-pentanoic acid {5-[1-(3-chloro-benzylamino)-ethyl]-[1,3,4]thiadiazol-2-yl}-amide HCl salt, LC-MS, RT=2.2 min, M+1=521.9

EXAMPLE 10

2-[2-(3,5-Difluoro-phenyl)-acetylamino]-N-[5-(3-hydroxy-1,1-dimethyl-propyl)-[1,3,4]thiadiazol-2-yl]-butyramide A mixture of 2-[2-(3,5-difluoro-phenyl)-acetylamino]-N-[5-(1,1-dimethyl-3-oxo-propyl)-[1,3,4]thiadiazol-2-yl]-butyramide (100 mg) and sodium borohydride (40 mg) in methanol was stirred at rt for 5 min. The mixture was quenched with water, extracted with methylene chloride. The organic layer was separated, dried, filtered and concentrated to give 90 mg of the tilte compound that was purified by silica gel column chromatography using hexane/EtOAc=3/2 to EtOAc as eluent to give 80 mg of the title compound, LC-MS RT=2.1 min, M+1=426.9

The following examples were prepared by the method analogous to that described in Example 10 starting from an appropriate aldehyde or ketone with excess of sodium borohydride in methanol.

2-[2-(3,5-Difluoro-phenyl)-acetylamino]-pentanoic acid [5-(3-hydroxy-1,1-dimethyl-propyl)-[1,3,4]thiadiazol-2-yl]-amide, LC-MS RT=2.2 min, M+1=440.9

2-[2-(3,5-Difluoro-phenyl)-acetylamino]-pentanoic acid [5-(1-hydroxy-ethyl)-[1,3,4]thiadiazol-2-yl]-amide LC-MS RT=1.9 min, M+1=398.9

EXAMPLE 11

2-[2-(3,5-Difluoro-phenyl)-acetylamino]-pentanoic acid [5-(1,1-dimethyl-2-morpholin-4-yl-ethyl)-[1,3,4]thiadiazol-2-yl]-amide A mixture of 2-[2-(3,5-Difluoro-phenyl)-acetylamino]-pentanoic acid [5-(1,1-dimethyl-2-oxo-ethyl)-[1,3,4]thiadiazol-2-yl]-amide (41 mg), morpholine (25 mg), acetic acid (0.02 ml) in methylene chloride (1 ml) was stirred at room temperature for 1 hr, and sodium triacetoxyborohydride (42 mg) was added. The mixture was stirred at room temperature for at least two days. The mixture was quenched with diluted NaOH and extracted with methylene chloride. The organic layer was separated, concentrated to dryness and the residue was purified by silica gel column chromatography using 35% to 65% ethyl acetate in hexane as eluent to give the title compound. The title compound was prepared as the corresponding HCl salt by adding HCl/doxane, followed by concentration to give a solid. LC_MS retention time 1.7 min M+1=497.0, M−1=495.0.

EXAMPLE 12

2-[2-(3,5-Difluoro-phenyl)-acetylamino]-pentanoic acid [5-(1,1-dimethyl-2-pyrrolidin-1-yl-ethyl)-[1,3,4] thiadiazol-2-yl]-amide A mixture of 2-[2-(3,5-Difluoro-phenyl)-acetylamino]-pentanoic acid [5-(1,1-dimethyl-2-oxo-ethyl)-[1,3,4]thiadiazol-2-yl]-amide (22 mg), pyrrolidine (0.02 ml), acetic acid (0.01 ml) in methylene chloride (1 ml) was stirred at room temperature for 1 hr, and sodium triacetoxyborohydride (28 mg) was added. The mixture was stirred at room temperature for at least two days. The mixture was quenched with diluted NaOH and extracted with methylene chloride. The organic layer was separated, concentrated to dryness and the residue was purified by silica gel column chromatography using 35% to 65% ethyl acetate in hexane as eluent to give the title compound. The title compound was prepared as the corresponding HCl salt by adding HCl/doxane, followed by concentration to give a solid. LC_MS retention time 2.0 min M+1=480.0.

Preparation A 1-(5-tert-Butyl-[1,3,4]thiadiazol-2-ylcarbamoyl)-butyl]-carbamic Acid tert-butyl Ester A mixture of 2-tert-butoxycarbonylamino-pentanoic acid (5.432 g, 25 mmol.), 5-tert-butyl-[1,3,4]thiadiazol-2-ylamine (3.925 g, 25 mmol), HBOT (3.540 g, 26.25 mmol), EDC HCl (5.73 g, 30 mmol.) and triethylamine (14 ml) in methylene chloride was stirred at room temperature until product formation or disappearance of starting material. The mixture was quenched with water and extracted with methylene chloride. The organic layer was separated, washed with dilute HCl, brine, dried over sodium sulfate and the solvent was removed at reduced pressure to provide the title compound (9.2671 g), LC-MS M+1=357.2.

The following examples were prepared by the method analogous to that in Preparation A.

[1-(5-Methyl-[1,3,4]thiadiazol-2-ylcarbamoyl)-butyl]-carbamic acid tert-butyl ester, M+1=315.4, 1H NMR (CDCl3) d 6.6(d,1H,NH), 4.4(m,1H), 2.7(s,3H), 1.2-1.9(m, 4H), 1.3(s,9H), 0.95(t,3H) ppm.

[1(5-Cyclopropyl-[1,3,4]thiadiazol-2-ylcarbamoyl)-butyl]-carbamic acid tert-butyl ester, M+1=341.3

[1-(5-Ethyl-[1,3,4]thiadiazol-2-ylcarbamoyl)-butyl]-carbamic acid tert-butyl ester, M+1=329.4, 1H NMR(CDCl3) d 7.0(s,1H,NH), 4.4(m,1H), 3.06(q,2H), 1.3-1.9(m,4H), 1.4(t, 3H), 1.28(s,9H), 0.94(t,3H) ppm.

[1-(5-tert-Butyl-[1,3,4]thiadiazol-2-ylcarbamoyl)-butyl]-carbamic acid tert-butyl ester, LC-MS M+1=357.2

{1-[5-(1,1-Dimethyl-butyl-[1,3,4]thiadiazol-2-ylcarbamoyl]-butyl}-carbamic acid tert-butyl ester, LC-MS RT=2.9 min, M+1=385.5

{1-[5-(1,1-Dimethyl-but-3-enyl)-[1,3,4]thiadiazol-2-ylcarbamoyl]-butyl}-carbamic acid tert-butyl ester, LC-MS RT=2.8 min, M+1=383.4

{1-[5-(1,1-Dimethyl-but-3-enyl)-[1,3,4]thiadiazol-2-ylcarbamoyl]-propyl}-carbamic acid tert-butyl ester, LC-MS RT=2.6 min, M+1=369.4

Preparation B

2-Amino-pentanoic Acid (5-tert-butyl-[1,3,4]thiadiazol-2-yl)-amide

A mixture of [1-(5-tert-butyl-[1,3,4]thiadiazol-2-ylcarbamoyl)-butyl]-carbamic acid tert-butyl ester (8.9 g) in dioxane (60 ml) was treated with 4 N HCl in 1,4-dioxane (20 ml). The mixture was stirred at rt overnight, then concentrated to dryness and pumped in vacuo to give the title compounds as a white solid (7.0908 g, 93%), APCI M+1=257.4

The following examples were prepared by the method analogous to that described in Preparation B.

2-Amino-pentanoic acid (5-methyl-[1,3,4]thiadiazol-2-yl)-amide, M+1=215.3

2-Amino-pentanoic acid (5-ethyl-[1,3,4]thiadiazol-2-yl-amide, M+1=229.3

2-Amino-pentanoic acid (5-cyclopropyl-[1,3,4]thiadiazol-2-yl)-amide, 1H NMR (CDCl3) d 4.15 (m,1H), 2.4(m,1H), 1.95(m,2H), 1.5(m,2H), 1.2-1.35(m,2H), 1.29(m,2H), 0.98(t, 3H) ppm.

2-Amino-pentanoic acid [5-(1,1-dimethyl-butyl)-[1,3,4]thiadiazol-2-yl]-amide, 1H NMR (CDCl3) d 4.14 (m,1H), 1.95(m,2H), 1.7(m,2H), 1.5(m,2H), 1.45(s,6H), 1.25(m,2H), 1.01(t,3H), 0.89(t,3H) ppm.

Based on a reading of the present description and claims, certain modifications to the compounds, compositions and methods described herein will be apparent to one of ordinary skill in the art. The claims appended hereto are intended to encompass these modifications.

What is claimed is:

1. A compound of the formula I-A

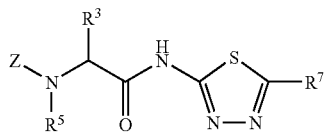

I-A wherein Z is selected from —C(=O)CHR$^1$R$^2$, —C(=S)CHR$^1$R$^2$, —(C=NR$^8$)CHR$^1$R$^2$, —C(=O)C(=O)R$^1$ and —S(O)$_2$—R$^1$;

R$^1$ is selected from —C$_1$-C$_{20}$ alkyl, —C$_2$-C$_{20}$ alkenyl, —C$_2$-C$_{20}$ alkynyl, —C$_1$-C$_{20}$ alkoxy, —C$_2$-C$_{20}$ alkenoxy, —C$_2$-C$_{20}$ alkynoxy, —C$_3$-C$_{20}$ cycloalkyl, —C$_4$-C$_{20}$ cycloalkenyl, (C$_{10}$-C$_{20}$)bi- or tricycloalkyl, (C$_{10}$-C$_{20}$) bi- or tricycloalkenyl, (4-20 membered) heterocycloalkyl, —C$_6$-C$_{20}$ aryl and (5-20 membered) heteroaryl;

wherein R$^1$ is optionally independently substituted with from one to six fluorine atoms or with from one to three substituents independently selected from the group R$^{1a}$;

R$^{1a}$ is in each instance independently selected from —OH, —C$_1$-C$_{12}$ alkyl, —C$_2$-C$_{12}$ alkenyl, —C$_2$-C$_{12}$ alkynyl, —C$_1$-C$_6$ alkoxy, —C$_2$-C$_6$ alkenoxy, —C$_2$-C$_6$ alkynoxy, —CF$_3$, —OCF$_3$, —Cl, —Br, —I, —ON, —NO$_2$, —NR$^9$R$^{10}$, —C(=O)NR$^9$R$^{10}$, —SO$_2$—NR$^9$R$^{10}$, —C(=O)R$^{11}$, —S(O)$_n$—R$^{11}$, —C$_3$-C$_{15}$cycloalkyl, —C$_4$-C$_{15}$ cycloalkenyl, —(C$_5$-C$_{11}$)bi- or tricycloalkyl, —(C$_7$-C$_{11}$)bi- or tricycloalkenyl, -(4-20 membered) heterocycloalkyl, —C$_6$-C$_{15}$ aryl, -(5-15 membered) heteroaryl, —C$_6$-C$_{15}$ aryloxy and -(5-15 membered) heteroaryloxy, wherein said cycloalkyl, cycloalkenyl, bi- or tricycloalkyl, bi- or tricycloalkenyl, heterocycloalkyl, aryl, heteroaryl, aryloxy and heteroaryloxy are each optionally independently substituted with from one to three substituents independently selected from the group R$^{1b}$;

R$^{1b}$ is in each instance independently selected from —OH, —C$_1$-C$_6$ alkyl, —C$_2$-C$_6$ alkenyl, —C$_2$-C$_6$ alkynyl, —C$_1$-C$_6$ alkoxy, —C$_2$-C$_6$ alkenoxy, —C$_2$-C$_6$ alkynoxy, —C$_1$-C$_6$ hydroxyalkyl, —F, —Cl, —Br, —I, —CN, —NO$_2$, —NR$^9$R$^{10}$, —C(=O)NR$^9$R$^{10}$, —C(=O)R$^{11}$, —S(O)$_n$—R$^{11}$, —C$_6$-C$_{15}$ aryloxy and -(5-15 membered) heteroaryloxy, wherein said alkyl, alkenyl and alkynyl are each optionally independently substituted with from one to six fluorine atoms or with from one to two substituents independently selected from —C$_1$-C$_4$ alkoxy, or with a hydroxy group;

R$^9$ and R$^{10}$ are in each instance each independently selected from —H, —C$_1$-C$_{12}$ alkyl, —C$_2$-C$_{12}$ alkenyl, —C$_{2-c12}$ alkynyl, —CF$_3$, —C(=O)R$^{11}$, —S(O)$_n$—R$^{11}$, —C(=O)OR$^{12}$, —C(=O)NR$^{11}$R$^{12}$, —SO$_2$—NR$^{11}$R$^{12}$, —(C$_{zero}$-C$_4$ alkylene)-(C$_3$-C$_{20}$ cycloalkyl), —(C$_{zero}$-C$_4$ alkylene)-(C$_4$-C$_8$ cycloalkenyl), —(C$_{zero}$-C$_4$ alkylene)-((C$_5$-C$_{11}$)bi- or tricycloalkyl), —(C$_{zero}$-C$_4$ alkylene)-((C$_7$-C$_{11}$)bi- or tricycloalkenyl), —(C$_{zero}$-C$_4$ alkylene)-((5-10 membered) heterocycloalkyl), (C$_{zero}$-C$_4$ alkylene)-(C$_6$-C$_{10}$ aryl) and —(C$_{zero}$-C$_4$ alkylene)-((5-10 membered) heteroaryl), wherein said aryl, heteroaryl, alkyl, alkenyl and alkynyl are each optionally independently substituted with from one to six fluorine atoms or with from one to two substituents independently selected from —C$_1$-C$_4$ alkoxy, or with a hydroxy group, and wherein said cycloalkyl, cycloalkenyl, bi-or tricycloalkyl, bi- or tricycloalkenyl, heterocycloalkyl, aryl and heteroaryl are each optionally independently substituted with from one to three substituents independently selected from —OH, —C$_1$-C$_{12}$ alkyl, —C$_2$-C$_{12}$ alkenyl, —C$_2$-C$_{12}$ alkynyl, —C$_1$-C$_6$ alkoxy, —C$_2$-C$_6$ alkenoxy, —C$_2$-C$_6$ alkynoxy, —C$_1$-C$_6$ hydroxyalkyl, —F, —Cl, —Br, —I, —CN, —NO$_2$, —CF$_3$, —NH$_2$, —C(=O)NH$_2$, —SO$_2$—NR$^9$R$^{10}$, —C(=O)H and —C(=O)OH, wherein said alkyl, alkenyl and alkynyl substituents are each optionally independently further substituted with from one to six fluorine atoms or with from one to two substituents independently selected from —C$_1$-C$_4$ alkoxy, or with a hydroxy group;

or NR$^9$R$^{10}$ may in each instance independently optionally form a heterocycloalkyl moiety of from four to ten ring members, said heterocycloalkyl moiety optionally containing one to two further heteroatoms independently selected from N, O and S, and optionally containing from one to three double bonds, wherein the carbon atoms of the heterocycloalkyl moiety of NR$^9$R$^{10}$ are optionally independently substituted with from one to three substituents independently selected from —OH, —C$_1$-C$_{12}$ alkyl, —C$_2$-C$_{12}$ alkenyl, —C$_2$-C$_{12}$ alkynyl, —C$_1$-C$_6$ alkoxy, —C$_2$-C$_6$ alkenoxy, —C$_2$-C$_6$ alkynoxy, —F, —Cl, —Br, —I, —CF$_3$, —NH$_2$, —C(=O)NH$_2$, —SO$_2$—NH$_2$, —C(=O)R$^{11}$, —S(O)$_n$—R$^{11}$, (C$_{zero}$-C$_4$ alkylene)-(C$_6$-C$_{10}$ aryl), (C$_{zero}$-C$_4$ alkylene)-((5-10 membered heteroaryl), (C$_{zero}$-C$_4$ alkylene)-(C$_6$-C$_{10}$ cycloalkyl) and (C$_{zero}$-C$_4$ alkylene)-((5-10 membered) heterocycloakyl, and wherein the (C$_{zero}$-C$_4$ alkylene)-((5-10 membered) heterocycloalkyl) substituent and the nitrogen atoms of said heterocycloalkyl moiety of NR$^9$R$^{10}$ are each optionally independently substituted with one substituent independently selected from —C$_1$-C$_{12}$ alkyl, —C$_2$-C$_{12}$ alkenyl, —C$_2$-C$_{12}$ alkynyl, —C(=O)NH$_2$, —SO$_2$NH$_2$, C(=O)R$^{11}$, —S(O)$_n$—R$^{11}$, (C$_{zero}$-C$_4$ alkylene)-(C$_6$-C$_{10}$ aryl), (C$_{zero}$-C$_4$ alkylene)-((5-10 membered) heteroaryl), —($C_{zero}$-$C_4$ alkylene)-($C_6$-$C_{10}$ cycloalkyl) and ($C_{zero}$-$C_4$ alkylene)-((5-10 membered) heterocycloalkyl), and wherein said alkyl, alkenyl and alkynyl substituents are each optionally independently further substituted with from one to six fluorine atoms, or with from one to two substituents independently selected from —$C_1$-$C_4$ alkoxy, or with a hydroxy group;

$R^{11}$ and $R^{12}$ are in each instance each independently selected from —$C_1$-$C_{15}$ alkyl, —$C_2$-$C_6$ alkenyl, —$C_2$-$C_6$ alkynyl, —($C_{zero}$-$C_4$ alkylene)-($C_3$-$C_{15}$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkenyl), —($C_{zero}$-$C_4$ alkylene)-($C_6$-$C_{15}$ aryl), —($C_{zero}$-$C_4$ alkylene)-((5-15 membered) heterocycloalkyl) and —($C_{zero}$-$C_4$ alkylene)-((5-15 membered) heteroaryl);

wherein $R^{11}$ and $R^{12}$ are each optionally independently substituted with from one to three substituents independently selected from the group consisting of: —OH, $C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$alkynoxy, —$C_1$-$C_6$ hydroxyalkyl, —F, —Cl, —Br, —I, —CN, $NO_2$, $C_6$-$C_{15}$ aryloxy and -(5-15 membered) heteroaryloxy, wherein said alkyl, alkenyl and alkynyl, are each optionally independently substituted with from one to six fluorine atoms or with from one to two substituents independently selected from $C_1$-$C_4$ alkoxy, or with a hydroxy group;

$R^2$ is selected from —H, —OH, —$NH_2$, —$CH_2OH$, —OC(=O)$CH_3$, —C($CH_3$)$_2$OH, —C($CH_3$)($CH_2OH_3$)(OH), —C(OH)($C_{zero}$-$C_4$ alkyl)($C_{zero}$-$C_4$ alkyl), —OC(=O)$R^4$ and —OC(=O)O$R^4$, wherein said —OC(=O)$R^4$ and —OC(=O)O$R^4$ may optionally be a prod rug of the corresponding OH of $R^2$;

$R^3$ is selected from —$C_1$-$C_6$ alkyl, —$C_2$-$C_6$ alkenyl, —$C_2$-$C_6$ alkynyl and —($C_{zero}$-$C_4$ alkylene)-($C_3$-$C_6$ cycloalkyl), wherein when $R^3$ is alkyl, alkenyl or alkynyl, $R^3$ is optionally independently substituted with a substituent independently selected from —$C_1$-$C_4$ alkoxy, —OH and —F;

$R^4$ is selected from —$C_1$-$C_4$ alkyl, —CH(OH)($C_1$-$C_4$ alkyl), —CH(OH)($C_5$-$C_6$ aryl), —CH(OH)((5-6 membered) heteroaryl), —CH(OH)($C_5$-$C_6$ cycloalkyl), and —CH(OH)((5-6 membered) heterocycloalkyl);

$R^5$ is selected from —H, —$C_1$-$C_4$ alkyl, —$C_2$-$C_4$ alkenyl, —$C_2$-$C_4$ alkynyl, —C(=O)($C_1$-$C_4$ alkyl), —$C_6$-$C_{10}$ aryl, -(5-20 membered) heteroaryl, —$SO_2$-($C_6$-$C_{10}$ aryl), —$SO_2$-((5-20 membered) heteroaryl), —$SO_2$—$CH_2$-($C_6$-$C_{20}$ aryl) and —$SO_2$—$CH_2$-((5-20 membered) heteroaryl);

$R^7$ is selected from $C_1$-$C_{20}$ alkyl, —($C_{zero}$-$C_4$ alkylene)-($C_3$-$C_{20}$ cycloalkyl), —($C_{zero}$-$C_4$ alkylene)-($C_4$-$C_{20}$ cycloalkenyl), —($C_{zero}$-$C_4$ alkylene)-(($C_{10}$-$C_{20}$)bi- or tricycloalkyl), —($C_{zero}$-$C_4$ alkylene)-(($C_{10}$-$C_{20}$)bi- or tricycloalkenyl), —($C_{zero}$-$C_4$ alkylene)-((3-20 membered) heterocycloalkyl), —($C_{zero}$-$C_4$ alkylene)-($C_6$-$C_{15}$ aryl) and —($C_{zero}$-$C_4$ alkylene)-((5-15 membered) heteroaryl), wherein said heterocycloalkyl optionally contains from one to four double or triple bonds;

wherein $R^7$ optionally substituted with from one to six fluorine atoms or with from one to three substituents independently selected from the group $R^{1a}$;

$R^8$ is selected from —H and —$C_1$-$C_6$ alkyl;

or, when Z is —C(=$NR^8$)CH$R^1R^2$, $R^8$ and $R^1$ may together with the nitrogen and carbon atoms to which they are respectively attached optionally form a five to fourteen membered heteroaryl ring or a five to eight membered heterocycloalkyl ring, wherein said heteroaryl or heterocycloalkyl ring optionally contains from one to two further heteroatoms selected from N, O and S, and wherein said heterocycloalkyl ring optionally contains from one to three double bonds, and wherein said heteroaryl or heterocycloalkyl ring is optionally substituted with from one to three substituents independently selected from the group $R^{1b}$; and n is 0, 1, 2; or a pharmaceutically acceptable salt thereof.

2. A compound according to claim 1, wherein R is —H, —OH, or —OC(=O)$CH_3$, or a pharmaceutically acceptable salt thereof.

3. A compound according to claim 2, wherein $R^2$ is —OH, or a pharmaceutically acceptable salt thereof.

4. A compound according to claim 1, wherein R is selected from —$C_1$-$C_{20}$ alkyl, —$C_2$-$C_{20}$ alkenyl, —$C_2$-$C_{20}$ alkynyl, —$C_3$-$C_{20}$ cycloalkyl, (4-20 membered) heterocycloalkyl, —$C_6$-$C_{20}$ aryl and (5-20 membered) heteroaryl; or a pharmaceutically acceptable salt thereof.

5. A compound according to claim 1, wherein:

Z is —C(=O)CH$R^1R^2$;

$R^1$ is —$C_1$-$C_{20}$ alkyl; and $R^2$ is —H, —OH or OC(=O)$CH_3$; or a pharmaceutically acceptable salt thereof.

6. A compound according to claim 5, wherein $R^2$ is —H or —OH; or a pharmaceutically acceptable salt thereof.

7. A compound according to claim 6, wherein $R^2$ is —OH; or a pharmaceutically acceptable salt thereof.

8. A compound according to claim 1, wherein:

Z is —C(=O)CH$R^1R^2$;

$R^1$ is —$C_1$-$C_{20}$ alkyl;

$R^2$ is —H, —OH or OC(=O)$CH_3$;

$R^3$ is —$C_1$-$C_6$alkyl;

$R^5$ is —H; and $R^7$ is —$C_1$-$C_{20}$ alkyl; or a pharmaceutically acceptable salt thereof.

9. A compound according to claim 8, wherein $R^2$ is —OH; or a pharmaceutically acceptable salt thereof.

10. A compound according to claim 8, wherein:

$R^1$ is —C($CH_3$)$_3$;

$R^2$ is —OH;

$R^3$ is —$CH_2CH_2CH_3$; and $R^7$ is —C($CH_3$)$_3$; or a pharmaceutically acceptable salt thereof.

11. A compound of formula

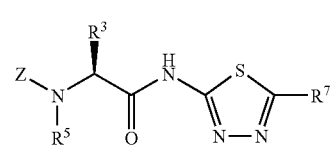

wherein Z is selected from —C(=O)CH$R^1R^2$, —C(=S)CH$R^1R^2$, —(C=$NR^8$)CH$R^1R^2$, —C(=O)C(=O)$R^1$ and —S(O)$_2$—$R^1$;

$R^1$ is selected from —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_2$-$C_{20}$ alkynoxy, —$C_3$-$C_{20}$ cycloalkyl, —$C_4$-$C_{20}$ cycloalkenyl, ($C_{10}$-$C_{20}$)bi- or tricycloalkyl, ($C_{10}$-$C_{20}$) bi- or tricycloalkenyl, (4-20 membered) heterocycloalkyl, —$C_6$-$C_{20}$ aryl and (5-20 membered) heteroaryl;

wherein $R^1$ is optionally independently substituted with from one to six fluorine atoms or with from one to three substituents independently selected from the group $R^{1a}$;

$R^{1a}$ is in each instance independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —$CF_3$, —$OCF_3$, —Cl, —Br, —I, —ON, —$NO_2$, —$NR^9R^{10}$, —$C(=O)NR^9R^{10}$, —$SO_2$—$NR^9R^{10}$, —$C(=O)R^{11}$, —$S(O)_n$—$R^{11}$, —$C_3$-$C_{15}$cycloalkyl, —$C_4$-$C_{15}$ cycloalkenyl, —($C_5$-$C_{11}$)bi- or tricycloalkyl, —($C_7$-$C_{11}$)bi- or tricycloalkenyl, -(4-20 membered) heterocycloalkyl, —$C_6$-$C_{15}$ aryl, -(5-15 membered) heteroaryl, —$C_6$-$C_{15}$ aryloxy and -(5-15 membered) heteroaryloxy, wherein said cycloalkyl, cycloalkenyl, bi- or tricycloalkyl, bi- or tricycloalkenyl, heterocycloalkyl, aryl, heteroaryl, aryloxy and heteroaryloxy are each optionally independently substituted with from one to three substituents independently selected from the group $R^{1b}$;

$R^{1b}$ is in each instance independently selected from —OH, —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —$NO_2$, —$NR^9R^{10}$, —$C(=O)NR^9R^{10}$, —$C(=O)R^{11}$, —$S(O)_n$—$R^{11}$, —$C_6$-$C_{15}$ aryloxy and -(5-15 membered) heteroaryloxy, wherein said alkyl, alkenyl and alkynyl are each optionally independently substituted with from one to six fluorine atoms or with from one to two substituents independently selected from —$C_1$-$C_4$ alkoxy, or with a hydroxy group;

$R^9$ and $R^{10}$ are in each instance each independently selected from —H, —$C_1$-$C_{12}$ alkyl, —$C_2$-$C_{12}$ alkenyl, —$C_2$-$C_{12}$ alkynyl, —$CF_3$, —$C(=O)R^{11}$, —$S(O)_n$—$R^{11}$, —$C(=O)OR^{12}$, —$C(=O)NR^{11}R^{12}$, —$SO_2$—$NR^{11}R^{12}$, —($C_{zero}$-$C_4$ alkylene)-($C_3$-$C_{20}$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkyl), —($C_{zero}$-$C_4$ alkylene)-((5-10 membered) heterocycloalkyl), ($C_{zero}$-$C_4$ alkylene)-($C_6$-$C_{10}$ aryl) and —($C_{zero}$-$C_4$ alkylene)-((5-10 membered) heteroaryl), wherein said aryl, heteroaryl, alkyl, alkenyl and alkynyl are each optionally independently substituted with from one to six fluorine atoms or with from one to two substituents independently selected from —$C_1$-$C_4$ alkoxy, or with a hydroxy group, and wherein said cycloalkyl, cycloalkenyl, bi-or tricycloalkyl, bi- or tricycloalkenyl, heterocycloalkyl, aryl and heteroaryl are each optionally independently substituted with from one to three substituents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —$NO_2$, —$CF_3$, —$NH_2$, —$C(=O)NH_2$, —$SO_2$—$NR^9R^{10}$, —$C(=O)H$ and —$C(=O)OH$, wherein said alkyl, alkenyl and alkynyl substituents are each optionally independently further substituted with from one to six fluorine atoms or with from one to two substituents independently selected from —$C_1$-$C_4$ alkoxy, or with a hydroxy group;

or $NR^9R^{10}$ may in each instance independently optionally form a heterocycloalkyl moiety of from four to ten ring members, said heterocycloalkyl moiety optionally containing one to two further heteroatoms independently selected from N, O and S, and optionally containing from one to three double bonds, wherein the carbon atoms of the heterocycloalkyl moiety of $NR^9R^{10}$ are optionally independently substituted with from one to three substituents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —F, —Cl, —Br, —I, —$CF_3$, —$NH_2$, —$C(=O)NH_2$, —$SO_2$—$NH_2$, —$C(=O)R^{11}$, —$S(O)_n$—$R^{11}$, ($C_{zero}$-$C_4$ alkylene)-($C_6$-$C_{10}$ aryl), ($C_{zero}$-$C_4$ alkylene)-((5-10 membered) heteroaryl), ($C_{zero}$-$C_4$ alkylene)-($C_6$-$C_{10}$ cycloalkyl) and ($C_{zero}$-$C_4$ alkylene)-((5-10 membered) heterocycloakyl, and wherein the ($C_{zero}$-$C_4$ alkylene)-((5-10 membered) heterocycloalkyl) substituent and the nitrogen atoms of said heterocycloalkyl moiety of $NR^9R^{10}$ are each optionally independently substituted with one substituent independently selected from —$C_1$-$C_{12}$ alkyl, —$C_2$-$C_{12}$ alkenyl, —$C_2$-$C_{12}$ alkynyl, —$C(=O)NH_2$, —$SO_2$—$NH_2$, $C(=O)R^{11}$, —$S(O)_n$—$R^{11}$, ($C_{zero}$-$C_4$ alkylene)-($C_6$-$C_{10}$ aryl), ($C_{zero}$-$C_4$ alkylene)-((5-10 membered) heteroaryl), —($C_{zero}$-$C_4$ alkylene)-($C_6$-$C_{10}$ cycloalkyl) and ($C_{zero}$-$C_4$ alkylene)-((5-10 membered) heterocycloalkyl), and wherein said alkyl, alkenyl and alkynyl substituents are each optionally independently further substituted with from one to six fluorine atoms, or with from one to two substituents independently selected from —$C_1$-$C_4$ alkoxy, or with a hydroxy group;

$R^{11}$ and $R^{12}$ are in each instance each independently selected from —$C_1$-$C_{15}$ alkyl, —$C_2$-$C_6$ alkenyl, —$C_2$-$C_6$ alkynyl, —($C_{zero}$-$C_4$ alkylene)-($C_3$-$C_{15}$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkyl), —($C_{zero}$-$C_4$ alkylene)-($C_6$-$C_{15}$ aryl), —($C_{zero}$-$C_4$ alkylene)-((5-15 membered) heterocycloalkyl) and —($C_{zero}$-$C_4$ alkylene)-((5-15 membered) heteroaryl);

wherein $R^{11}$ and $R^{12}$ are each optionally independently substituted with from one to three substituents independently selected from the group consisting of: —OH, $C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$alkynoxy, —$C_1$-$C_6$ hydroxyalkyl, —F, —Cl, —Br, —I, —CN, $NO_2$, $C_6$-$C_{15}$ aryloxy and -(5-15 membered) heteroaryloxy, wherein said alkyl, alkenyl and alkynyl, are each optionally independently substituted with from one to six fluorine atoms or with from one to two substituents independently selected from $C_1$-$C_4$ alkoxy, or with a hydroxy group;

$R^2$ is selected from —H, —OH, —$NH_2$, —$CH_2OH$, —$OC(=O)CH_3$, —$C(CH_3)_2OH$, —$C(CH_3)(CH_2COH_3)(OH)$, —$C(OH)(C_{zero}$-$C_4$ alkyl)($C_{zero}$-$C_4$ alkyl), —$OC(=O)R^4$ and —$OC(=O)OR^4$, wherein said —$OC(=O)R^4$ and —$OC(=O)OR^4$ may optionally be a prodrug of the corresponding OH of $R^2$;

$R^3$ is selected from —$C_1$-$C_6$ alkyl, —$C_2$-$C_6$ alkenyl, —$C_2$-$C_6$ alkynyl and —($C_{zero}$-$C_4$ alkylene)-($C_3$-$C_6$ cycloalkyl), wherein when $R^3$ is alkyl, alkenyl or alkynyl, $R^3$ is optionally independently substituted with a substituent independently selected from —$C_1$-$C_4$ alkoxy, —OH and —F;

$R^4$ is selected from —$C_1$-$C_4$ alkyl, —$CH(OH)(C_1$-$C_4$ alkyl), —$CH(OH)(C_5$-$C_6$ aryl), —$CH(OH)((5-6 $ membered) heteroaryl), —$CH(OH)(C_5$-$C_6$ cycloalkyl), and —$CH(OH)((5-6$ membered) heterocycloalkyl);

$R^5$ is selected from —H, —$C_1$-$C_4$ alkyl, —$C_2$-$C_4$ alkenyl, —$C_2$-$C_4$ alkynyl, —$C(=O)(C_1$-$C_4$ alkyl), —$C_6$-$C_{10}$ aryl, -(5-20 membered) heteroaryl, —$SO_2$-($C_6$-$C_{10}$ aryl), —$SO_2$-((5-20 membered) heteroaryl), —$SO_2$—$CH_2$—($C_6$-$C_{20}$ aryl) and —$SO_2$—$CH_2$-((5-20 membered) heteroaryl);

$R^7$ is selected from $C_1$-$C_{20}$ alkyl, —($C_{zero}$-$C_4$ alkylene)-($C_3$-$C_{20}$ cycloalkyl), —($C_{zero}$-$C_4$ alkylene)-($C_4$-$C_{20}$ cycloalkenyl), —($C_{zero}$-$C_4$ alkylene)-(($C_{10}$-$C_{20}$)bi- or tricycloalkyl), —($C_{zero}$-$C_4$ alkylene)-(($C_{10}$-$C_{20}$)bi- or tricycloalkenyl), —($C_{zero}$-$C_4$ alkylene)-((3-20 membered) heterocycloalkyl), —($C_{zero}$-$C_4$ alkylene)-($C_6$-$C_{15}$ aryl) and —($C_{zero}$-$C_4$ alkylene)-((5-15 membered) heteroaryl), wherein said heterocycloalkyl optionally contains from one to four double or triple bonds;

wherein $R^7$ optionally substituted with from one to six fluorine atoms or with from one to three substituents independently selected from the group $R^{1a}$;

$R^8$ is selected from —H and —$C_1$-$C_6$ alkyl;

or, when Z is —C(=$NR^8$)$CHR^1R^2$, $R^8$ and $R^1$ may together with the nitrogen and carbon atoms to which they are respectively attached optionally form a five to fourteen membered heteroaryl ring or a five to eight membered heterocycloalkyl ring, wherein said heteroaryl or heterocycloalkyl ring optionally contains from one to two further heteroatoms selected from N, O and S, and wherein said heterocycloalkyl ring optionally contains from one to three double bonds, and wherein said heteroaryl or heterocycloalkyl ring is optionally substituted with from one to three substituents independently selected from the group $R^{1b}$; and n is 0, 1, 2; or a pharmaceutically acceptable salt thereof.

12. A compound according to claim 11, wherein $R^2$ is —H, —OH, or —OC(=O)$CH_3$, or a pharmaceutically acceptable salt thereof.

13. A compound according to claim 12, wherein $R^2$ is —OH, or a pharmaceutically acceptable salt thereof.

14. A compound according to claim 11, wherein $R^1$ is selected from —$C_1$-$C_{20}$ alkyl, —$C_2$-$C_{20}$ alkenyl, —$C_2$-$C_{20}$ alkynyl, —$C_3$-$C_{20}$ cycloalkyl, (4-20 membered) heterocycloalkyl, —$C_6$-$C_{20}$ aryl and (5-20 membered) heteroaryl; or a pharmaceutically acceptable salt thereof.

15. A compound according to claim 11, wherein:
Z is —C(=O)$CHR^1R^2$;
$R^1$ is —$C_1$-$C_{20}$ alkyl; and
$R^2$ is —H, —OH or OC(=O)$CH_3$; or
a pharmaceutically acceptable salt thereof.

16. A compound according to claim 15, wherein $R^2$ is —H or —OH; or a pharmaceutically acceptable salt thereof.

17. A compound according to claim 16, wherein $R^2$ is —OH; or a pharmaceutically acceptable salt thereof.

18. A compound according to claim 11, wherein:
Z is —C(=O)$CHR^1R^2$;
$R^1$ is —$C_1$-$C_{20}$alkyl;
$R^2$ is —H, —OH or OC(=O)$CH_3$;
$R^3$ is —$C_1$-$C_6$alkyl;
$R^5$ is —H; and
$R^7$ is —$C_1$-$C_{20}$ alkyl; or
a pharmaceutically acceptable salt thereof.

19. A compound according to claim 18, wherein:
$R^1$ is —C($CH_3$)$_3$;
$R^2$ is —OH;
$R^3$ is —$CH_2CH_2CH_3$; and
$R^7$ is —C($CH_3$)$_3$; or
a pharmaceutically acceptable salt thereof.

* * * * *